United States Patent [19]
Van Embden et al.

[11] Patent Number: 6,074,820
[45] Date of Patent: Jun. 13, 2000

[54] DETECTION AND DIFFERENTIATION OF MYCOBACTERIUM TUBERCULOSIS COMPLEX BACTERIA BY DIRECT VARIANT REPEAT OLIGOTYPING

[75] Inventors: Johannes Dirk Anthonie Van Embden, Utrecht; Leendert Marinus Schouls, Wijk Bij Duurstede; Judith Kamerbeek, Utrecht, all of Netherlands

[73] Assignee: De Staat der Nederlanden, Vertegenwoordigd door de Minister van Welzijn, Volksgezondhed en Cultuur, Rijswijk, Netherlands

[21] Appl. No.: 08/737,607

[22] PCT Filed: May 16, 1994

[86] PCT No.: PCT/NL94/00110

§ 371 Date: Jan. 22, 1997

§ 102(e) Date: Jan. 22, 1997

[87] PCT Pub. No.: WO95/31569

PCT Pub. Date: Nov. 23, 1995

[51] Int. Cl.$^7$ .............................. C12Q 1/68; C07H 21/04; C12P 19/34

[52] U.S. Cl. ........................... 435/6; 435/91.2; 536/24.3; 536/24.32

[58] Field of Search ..................... 435/91.2, 6; 536/24.3, 536/24.32

[56] References Cited

U.S. PATENT DOCUMENTS 4,683,195  7/1987  Mullis et al. ............................... 435/6

FOREIGN PATENT DOCUMENTS

WO 93/08297  4/1993  WIPO .

OTHER PUBLICATIONS

P.W.M. Hermans, et al., "Characterization of a major poly–morphic tandem repeat in *Mycobacterium tuberculosis* and its potential use in the epidemiology of *Mycobacterium kansaii* and *Mycobacterium gordonae*", *Journal of Bacteriology*, vol. 174, No. 12, Jun. 1992, Baltimore, pp. 4157–4165.

T.J. Doran et al., "Characterization of a highly repeated DNA sequence from *Mycrobacterium bovis*", *FEMS Microbiology Letters*, vol. 111, No. 2+3, Aug. 1993, Amsterdam, Netherlands, pp. 147–152.

J. Versalovic et al., "Distribution of repetitive DNA sequences in eubacteria and application to fingerprinting of bacterial genomes", *Nucleic Acids Research*, vol. 19, No. 24, Dec. 1991, Oxford, England, pp. 6823–6831.

P.M.A. Groenen et al., "Nature of DNA polymorphism in the direct repeat cluster of *Mycobacterium tuberculosis*, application for strain differentiation by a novel typing method", *Molecular Microbiology*, vol. 10, No. 5, May 1993, Oxford, United Kingdom, pp. 1057–1065.

P. Palittapongarnpim et al., "DNA fingerprinting of *Mycobacterium tuberculosis* isolates by ligation–mediated polymerase chain reaction", *Nucleic Acids Research*, vol. 21, No. 3. Feb. 1993, oXFORD, eNGLAND, pp. 761–762.

P. Pallitapongarnpim et al., "DNA fragment length polymorphism analysis of *Mycobacterium tubercolosis* isolates by arbitrarily primed polymerase chain reaction", *Journal of Infectious Diseases*, vol. 167, No. 4, Apr. 1993, The University of Chicago, pp. 975–978.

P.W.M. Hermans et al., "Insertion element IS987 from Mycoacyterium bovis BCG is located in a hot–spot integration region for insertion elements in *Mycobacterium tuberculosis* complex strains", *Infection and Immunity*, vol. 59, No. 8, Aug. 1991, Baltimore, pp. 2695–2705.

A.J. Jeffreys et al., "Minisatellite repeat coding as a digital approach to DNA typing", *Nature*, vol. 354, Nov. 1991, London, United Kingdom, pp. 204–209.

D. Van Soolingen et al., "Comparison of Various Repetitive DNA Elements as Genetic Markers for Strain Differentiation and Epidemiology of *Mycobacterium tuberculosis*", *Journal Of Clinical Microbiology*, vol. 31, No. 8, Aug. 1993, pp. 1987–1995.

D. Van Soolingen et al., "Insertion Element IS1081–Associated Restriction Fragment Length Polymorphisms in *Mycobacterium tuberculosis* Complex Species: a Reliable Tool for Recoognizing *Mycobacterium bovis* BCG", *Journal of Clinical Microbiology*, vol. 30, No. 7, Jul. 1992, pp. 1772–1777.

J.D.V. Van Embden et al., "Strain Identification of *Mycobacterium tuberculosis* by DNA Fingerprinting: Recommendations for a Standardized Methodology", *Journal of Clinical Microbiology*, vol. 31, No. 2, Feb. 1993, pp. 406–409.

P.W.M. Hermans et al., "Insertion Element IS987 from *Mycobacterium bovis* BCG is Located in a Hot–Spot Integration Region for Insertion Element in *Mycobacterium tuberculosis* Complex Strains", *Infection and Immunity*, vol. 59, No. 8, Aug. 1991, pp. 2695–2705.

J.D.A. Van Embden et al., "Genetic markers for the epidemiology of tuberculosis", *Mycobacteria and Aids*, pp. 385–391.

P.M.A. Groenen et al., "Nature of DNA polymorphism in the direct repeat cluster of *Mycobacterium tuberculosis* ; application for strain differentiation by a novel typing method", *Molecular Microbiology*, vol. 10, No. 5, 1993, pp. 1057–2065.

*Primary Examiner*—Ardin H. Marschel
*Assistant Examiner*—Joyce Tung
*Attorney, Agent, or Firm*—Young & Thompson

[57] ABSTRACT

A method and primary pair and kit for the in vitro amplification of nucleic acid using amplification primers in amplification reactions. There is used a pair of primers comprising oligonucleotide sequences complementary to a part of a Direct Repeat sequence of a microorganism belonging to the *M tuberculosis* complex of microorganisms, whereby hybridization to a Direct Repeat occurs and subsequently elongation of the hybridized primer takes place. The primers are such that elongation in the amplification reaction occurs for one primer in a 5' direction and for the other primer in a 3' direction.

20 Claims, 8 Drawing Sheets fig-2
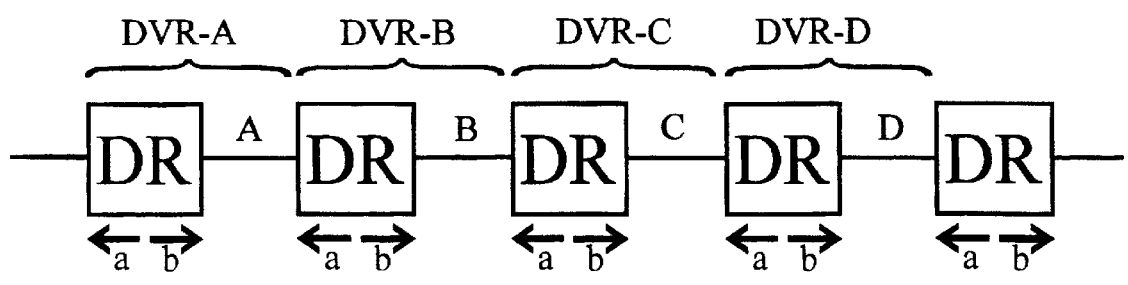
amplification products:
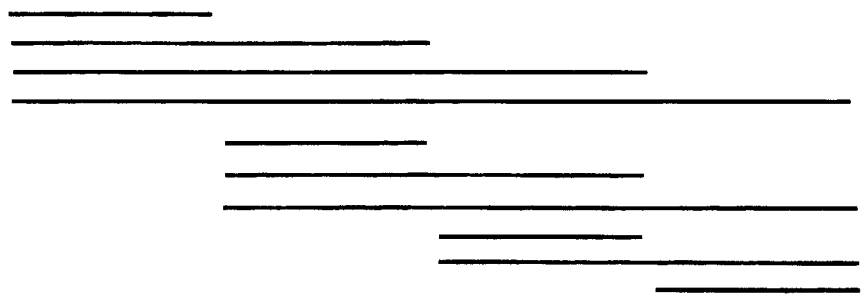

Fig-3-1

ACGCGTATATCGGTTTCCTACACCAGGATTCACGAGGGCACGCAACGTTGGCGAGCGACCTCATGGAGGTATGGCGG

GCGCCGATCATCGATGACACCGTACTTCGATTGATCGCGGACGGTGTGGTCGACACCCGGGCTTTCAGCAAGAACTC

CGACACGGGGCCGTCTTCGCGACACGGGAAGCCACACGATCCATCGCGCGCGCCTTTTGTAATCGAATCGCACGAA

CCGCCACCTACATCAAAGGCGATCCTTACCGATACACTTTTCAGTACGCCCTCGACTTGCAACTGCAAAGCTCGTGC

GTGTTATTCGAAGCCGGGGAACCCGTCGNGGTCGTCGATATCACCTCCGAGCCATCCGGAGCCTAAATGCCCACTCG

CAGCCGTGAGGAGTACTTCAATCTCCCGCTCAAAGTGGACGAGTCCAGCGGCACTATAGGCAAGATGTTCGTCCTCG

TAATATACGACATCAGCGACAACCGGCGGCGGGCTTCACTTGCGAAGATCCTGGCCGGGTTTGGCTATCGCGTCCAAG

AGTCCGCATTCGAAGCGATGCTGACGAAGGGCCAGCTCGCGAAACTAGTTGCACGTATCGACCGCTTCGCCATCGAC

TGCGACAACATCCGGATCTATAAGATAAGAGGTGTTGCGGCAGTTACGTTCTACGGAAGGGGACGGCTTGTCAGCGC

AGAGGAGTTTGTGTTCTTTTGACATCATCAGCAGGCATTGTTACCACACGCTGGACGAATTGTCCATAGA

<u>GTCGTCAGACCCAAAACCCCGAGAGGGGACGGAAAC</u>TTAAAACCGTGTTGTACTGCAACCCGGAATTCTTGAAC

<u>GTCGTCAGACCCAAAACCCCGAGAGGGGACGGAAAC</u>CATAGAGGGTCGCCGGTTCTGGATCACGCTCCCCTAGTCGT

<u>GTCGTCAGACCCAAAACCCCGAGAGGGGACGGAAAC</u>TTTTTGCCTCATAATTGGGCGACAGCTTTTGACCAA

<u>GTCGTCAGACCCAAAACCCCGAGAGGGGACGGAAAC</u>TCGCAAGCGCCGTGCTTCCAGTGATCGCCTTCTA

<u>GTCGTCAGACCCAAAACCCCGAGAGGGGACGGAAAC</u>AACACCTCAGTAGCACGTCATACGCCGACCAATCATCAG

<u>GTCGTCAGACCCAAAACCCCGAGAGGGGACGGAAAC</u>TTTTCTGACCACTTGTGCGGGATTAGCGGGCTTAG

<u>GTCGTCAGACCCAAAACCCCGAGAGGGGACGGAAAC</u>ACCAATGCGTCGTCATTTCCGGCTTCAATTTCAGCCT

<u>GTCGTCAGACCCAAAACCCCGAGAGGGGACGGAAAC</u>CTGAGGAGAGCGAGTACTCGGGGCTGCCGTCTGCGCTG

<u>GTCGTCAGACCCAAAACCCCGAGAGGGGACGGAAAC</u>GCGTGAAACCGCCCCCAGCCTCGCCGGGGCCGCCTAG

<u>GTCGTCAGACCCAAAACCCCGAGAGGGGACGGAAAC</u>ACTCGGAATCCCATGTGCTGACAGCGGATTCGCAT

<u>GTCGTCAGACCCAAAACCCCGAGAGGGGACGGAAAC</u>CGGGCAGCGTTCGACACCCGCTCTAGTTGACTTCCGG

<u>GTCGTCAGACCCAAAACCCCGAGAGGGGACGGAAAC</u>CAGGTGAGCAACGGCGGCGGCAACCTGGCGGCCACGGGTCG

<u>GTCGTCAGACCCAAAACCCCGAGAGGGGACGGAAAC</u>ATGGATATCTGCTGCCCGCCCGGGGAGATGCTGTCCGAG

<u>GTCGTCAGACCCAAAACCCCGAGAGGGGACGGAAAC</u>TTCGTCGACCATCATTGCCATTCCCTCTCCCCACGT

<u>GTCGTCAGACCCAAAACCCCGAGAGGGGACGGAAAC</u>TTGCGCCAACCCTTTCGGTGTGATGCGGATGGTCGGCTCGG

Fig-3-2

GTCGTCAGACCCAAAACCCCGAGAGGGGACGGAAACCTTGAATAACGCGCAGTGAATTTCGCGGA

TCAGACCCAAAACCCCGAGAGGGGACGGAAACATTCGCACGAGTTCCCGTCAGCGTCGTAAATCGCCA

GTCGTCAGACCCAAAACCCCGAGAGGGGACGGAAACCCGGCAACAATCGCGCCGGCCCGCGCGGATGACTCCG

GTCGTCAGACCCAAAACCCCGAGAGGGGACGGAAACCGCATGGACCCGGGCGAGCTGCAGATGGTCCGGGAG

GTCGTCAGACCCAAAACCCCGAGAGGGGACGGAAACTGGATTGCGCTAACTGGCTTGGCGCTGATCCTGGTG

GTCGTCAGACCCAAAACCCCGAGAGGGGACGGAAACTTGGAGCGTGTCACCGCAGACGGCACGATTGAGACAA

GTCGTCAGACCCAAAACCCCGAGAGGGGACGGAAACCCTCAGCTCAGCATCGCTGATGCGGTCCAGCTCGTCCGT

GTCGTCAGACCCAAAACCCCGAGAGGGGACGGAAACCCAACCTCACCGCCTGCTGGGTGAGACGTGCTCGCCGCGA

GTCGTCAGACCCAAAACCC

TGAACCGCCCCG....IS6110....GACTCACCGGGGCGGTTCA

3816CCCCGAGAGGGGACGGAAACTCGGGGAGCCGATCAGCGACCACCGCACCCTGTCA

GTCGTNAGACCCAAAACCCCGAGAGGGGACGGAAACCTTCAGCACCACCATCATCCGGCGCCTCAGCTCAGCAT

GTCGTCAGACCCAAAACCCCGAGAGGGGACGGAAACCCTTCGACGCCGGATTCGTGATCTCTTCCCGCGGATAG

GTCGTCAGACCCAAAACCCCGAGAGGGGACGGAAACTGCCCCGGCGTTTAGCGATCACAACACCAACTAATG

GTCGTCAGACCCAAAACCCCGAGAGGGGACGGAAACCAGCGAAATACAGGCTCCACGACACGACCACAACGC

GTCGTCAGACCCAAAACCCCGAGAGGGGACGGAAACTCTTGACGATGCGGTTGCCCCGCGCCCTTTTCCAGCC

GTCGTCAGACCCAAAACCCCGAGAGGGGACGGAAACAGGTTCGCGTCAGACAGGTTCGCGTCGATCAAGTCCG

GTCGTCAGACCCAAAACCCCGAGAGGGGACGGAAACTTTATCACTCCCGACCAAATAGGTATCGGCGTGTTCAA

GTCGTCAGACCCAAAACCCCGAGAGGGGACGGAAACATTTTGAGCGCGAACTCGTCCACAGTCCCCCTTTCAG

GTCGTCAGACCCAAAACCCCGAGAGGGGACGGAAACGCCCCGTGGATGGCGGATGCGTTGTGCGCGCAAGT

GTCGTCAGACCCAAAACCCCGAGAGGGGACGGAAACCCGACGATGGCCAGTAAATCGGCGTGGGTAACCGATCCGG

GTCGTCAGACCCAAAACCCCGAGAGGGGACGGAAACTAGTACGCCATCTGTGCCTCATACAGGTCCAGTGCCCT

GTCGTCAGACCCAAAACCCCGAGAGGGGACGGAAACCTGACGGCACGGAGCTTTCCGGCTTCTATCAGGTA

GTCGTCAGACCCAAAACCCCGAGAGGGGACGGAAACCCTCATGGTGGGACATGGACGAGCGCGACTATCGGG

GTCGTCGGACCCAAAACCCCGAGAGGGGACGGAAACTGGACGCAGAATCGCACCGGGTGCGGGAGGTGCAGCA

GTCGTCAGACCCAAAACCCCGAGAGGGGACGGAAACGCATATCGCCCGCCACACCACAGCCACGCTACTGCTCCAT

Fig-3-3

GTCCTCAGACCCAAAACCCCGAGAGGGGACGGAAACACACCGCCGATGACAGCTATGTCCGAGTGACATCCTCCCA

GTCGTCAGACCCAAAACCACGAGAGGGGACGGAAACTTGAACCGCCCTTCGCGCGGTGTTTCGGCCGTGCCCGA

GTCGTCAGACCCAAAACCCCGAGAGGGGACGGAAAC

TACGACGACTGGGTCGCCACCGCGTCTGTCGACCTNGCATTCAGGATGANCATGATGGCGGCGTTGACGGTGAGGAC

GTTTGGTCATGAAATGNNCNCGCCGGGAGATGTCCGGCGGGGTCGGTGGTGTTCGGGGTGTCGGTGTGGTGTTCAGT

CTGCCGTGACTTCGGCGATGGCGGTGCGGNTGGTGGATTCGTCGACGATGGCCTTNTCGGCGGCGAAGGCGGCGACG

AGGGCTTNCAGGGCGAGGTTGTTGACCGCGCGGGGGTAGCCCCGNCTGGTCTGGTGGATCAACCCGATGGCGTCGTC

GGAGAACAGGGCATCGTCGNGTCCGGCTANCTTNAGGTTGTTGCGTAGGTAGCTTCC

DETECTION AND DIFFERENTIATION OF MYCOBACTERIUM TUBERCULOSIS COMPLEX BACTERIA BY DIRECT VARIANT REPEAT OLIGOTYPING

INTRODUCTION

Tuberculosis is an infectious disease that yearly kills more people than any other single infectious disease. The WHO estimates that yearly about 10 million people contract tuberculosis and that 3 million people die from this disease (37). After a long period of slow decrease in incidence, tuberculosis is on the increase again in most Western countries. Furthermore, the emergence of multidrug-resistant *M. tuberculosis* strains and the association of tuberculosis and Human Immunodeficiency Virus infected individuals are worsening the situation dramatically (1, 2, 4, 6, 7, 10, 37).

One of the key factors in the control of tuberculosis is the rapid diagnosis of the disease and the identification of the sources of infection. *M. tuberculosis* strain typing has already proved to be extremely useful in outbreak investigations (6, 14, 33) and is being applied to a variety of epidemiologic questions in numerous laboratories. Traditionally, laboratory diagnosis is done by microscopy, culturing of the micro-organism, skin testing and X-ray imaging. Unfortunately, these methods are often not sensitive, not specific and are very time-consuming, due to the slow growth rate of *M. tuberculosis*. Therefore, new techniques like in vitro amplification of *M. tuberculosis* DNA have been developed to rapidly detect the micro-organism in clinical specimens (14). The ability to differentiate isolates of *M. tuberculosis* by DNA techniques has revolutionarized the potential to identify the sources of infection and to establish main routes of transmission and risk factors for acquiring tuberculosis by infection (1, 3–10, 14, 16, 19–22, 25, 26, 29–36). The use of an effective universal typing system will allow strains from different geographic areas to be compared and the movement of individual strains to be tracked. Such data may provide important insights and identify strains with particular problems such as high infectivity, high virulency and/or multi-drug resistance. Analysis of large numbers of isolates may provide answers to long-standing questions regarding the efficacy of BCG vaccination and the frequency of reactivation versus reinfection.

Because *M. tuberculosis* complex bacteria constitute a genetically remarkably homogenous group of bacteria, repetitive DNA elements and transposable elements, that are associated with genetic rearrangements of chromosomal DNA, have been exploited for strain differentiation of *M. tuberculosis*. Two of these are insertion sequences and the remainder are short repetitive DNA sequences with no known function or phenotype.

The most widely used element for strain differentiation is IS6110, a 1355 bp insertion sequence, which was initially identified in *M. tuberculosis* (19, 30) and subsequently found to be distributed through all *M. tuberculosis* complex bacteria, including *Mycobacterium bovis, Mycobacterium africanum, M. microti* and *bovis* BCG (11, 14, 15). Other elements to potentially differentiate *M. tuberculosis* include the Major Polymorphic Tandem Repeat (MPTR), the Polymorphic GC rich repetitive sequence (PGRS) and the Direct Repeat (DR) sequence (15, 16, 26).

Most methods described for strain differentiation of *M. tuberculosis* depend on the so-called Restriction Fragment Length Polymorphism (RFLP) observed by the technique of Southern blotting. This technique requires the purification of chromosomal DNA from cultured *M. tuberculosis* bacteria. In addition this method is not suited for detecting a large number of strains, i.e. strains containing only one IS6110 copy or no IS6110 copy (35) when IS6110 fingerprinting is carried out as the presence of multiple IS6110 units is required for RFLP. Virtually all *M. bovis* BCG strains as well as a number of strains from India (35) contain only a single IS copy. Most strains could however be differentiated by fingerprinting with the 36-bp direct repeat or the polymorphic GC-rich repetitive DNA-element. Less discriminative power was obtained with the major polymorphic tandem repeat and the insertion element IS1081. Furthermore the known techniques of fingerprinting are demanding in terms of costs, the technical skills, and the time needed to perform them successfully (32). Therefore, this way of "DNA fingerprinting" cannot be performed on a routine basis in most laboratories.

Although Polymerase Chain Reaction (PCR)-based methods have been developed to increase the speed of *M. tuberculosis* fingerprinting, the methods still need the purification of DNA from cultured cells and/or are technically demanding (12, 13, 23, 24, 27).

Groenen et al. (12) describe a method of strain differentiation based on the nature of the DNA polymorphism in the DR cluster enabling typing of individual *M. tuberculosis* strains in a single PCR. The described method was based on the genetic variation in the DR region and the PCR method used the primers SP24-R (derived from spacer region 24) and IS-L (derived from the IS copy) on the basis of the previously established partial sequence of the DR region in *M. bovis* BCG P3 (15). The sizes of the amplified products range from approximately 300 to 550 bp. Using this method it was illustrated that *M. bovis* strain 42 differs from *M. bovis* PCG P3 in the absence of a discrete DVR, namely DVR 26. *M. tuberculosis* strains H37Ra and H37Rv differed from the P3 strain in the absence of two discrete contiguous DVR's. DVR 25 and DVR 26. The three remaining *M. tuberculosis* isolates 1430 en 31 differed from *M. bovis* BCG p3 in the absence of a 262 bp stretch of DNA located directly left from the inverted repeat of IS6110 comprising DVR 27 to DVR 29, 15 bp of the unique spacer in DVR 26 and 18 bp of the DR in DVR 30. In the DVR-PCR method the method of Jeffreys et al. 1991 (17) was modified. In the Jeffreys et al. method designated as MVR-PCR or digital typing advantage is taken of a frequently occuring polymorphism of a single base pair in the 29 bp minisatelite repeat MS32. In the MVR-PCR two primer pairs are used each of which allows the amplification of MS32 multimers which either have an adenine (A) or a guanine (G) at the 5' terminus. Separation by electrophoresis of the amplified products allows the reading of the sequence of the MVR's containing either an A or G at the 5' end respectively. In the DVR-PCR method the polymorphism in the DR region mainly comprises the presence or absence of DVR's which like the MS32 minisateLlite are composed of a non-variant part (DR) and a variant part (the spacer sequence). The MVR-PCR method was modified to permit the selective amplification of multimers of DVR's containing either an A, C, G or T at the 5' end of the spacer at the junction with the DR. For this purpose four primer combinations were prepared to drive the four spacer specific PCR's. Each combination contained the reverse primer IS-L and either one of the four primers based on the DR sequence. These four primers designated DRA-R, DRC-R, DRG-R and DRT-R, respectively contained a sequence of 19 residues derived from the conserved DR sequence plus either one of the four bases at the 3' terminus. The principle of the method is shown in FIG. 3 of reference 12. Each of the four DVR specific primers results in a ladder of DVR multimers increasing inside from bottom to top. This results in a so-called first spacer residue sequence or FSR sequence.

Despite the excellent differentiation by DVR-PCR of the four strains analyzed in (12) the method has a number of disadvantages. The DNA sequence technique in the adapted version as described by Jeffreys et al. is technically extremely difficult. Often the ladder cannot be read very well and as small fragments amplify better than the larger fragments the ladder is often incomplete. Furthermore, the test cannot be carried out in a routine manner in a simple laboratory such as, for example, a hospital laboratory. Therefore, in practical hospital tests such a method cannot be used. Furthermore, apart from the sequencing problems a Southern blot is also required which involves a large amount of work. The practical problems associated with Southern blot hybridisation technique include the relatively complex nature of the method which requires multiple steps over a number of days and a lengthy delay from isolation of the organism to the DNA typing result, largely because of cultivation of the organism in liquid media for DNA extraction. A rapid and simple means of strain typing, based on PCR amplification would circumvent delays in obtaining a typing result and provide a relatively simply assay that could be performed in many laboratories. To have sufficient genomic DNA for fingerprinting the isolate has to be subcultured for 2 to 4 additional weeks after identification. In the setting of an outbreak especially one of multidrug-resistant tuberculosis (MDRTB) rapid identification of stains may enhance control efforts by detection and interruption of transmission chains.

In ref. 27 Ross and Dwyer disclose using the ends of the insertion sequence IS6110 as oligonucleotide primers in an attempt to amplify DNA between clusters of this element on the genome. This test is based on the assumption that the insertion sequence IS6110 is present in 1 to 19 copies on the genome and is located in different sites for various strains. They illustrate that the PCR amplification method disclosed produced no clear product for the two strains without IS6110 thereby illustrating the disadvantage of this method. Furthermore, Ross and Dwyer illustrate in their article that the PCR amplification using the ends of the insertion sequence IS6110 resulted in bands of various intensities, thereby illustrating the lack of reliability of the results of this test.

In ref. 13 a variant on the RFLP typing using the polymerase chain reaction with a primer specific for IS66110 is described wherein a second primer complementary to a linker ligated to the restricted genomic DNA is used. In one strand the linker contains uracil in place of thymidine and specific amplification is obtained by elimination of the strand with uracil-N-glycosylase. The same disadvantages for this method can be mentioned as for the previous PCR-DVR method.

In ref. 25 Palittapongarnpim et al. describe the use of PCR using arbitrary primers. In this article it is illustrated that the PCR banding patterns of the strains H37Rv and H37Ra are identical. They illustrated that arbitrarily primed PCR can distinguish strains of *M. tuberculosis* however the inability of APPCR to distinguish between the H37Rv and H37Ra strains demonstrates a limitation of the APPCR for closer related strains.

This invention describes a method to differentiate micro-organisms belonging to the *M. tuberculosis* complex by a robust method, which is rapid and simple. The method can be performed in a laboratory without sophisticated equipment and it can be carried out by technicians, who do not have to be trained in sophisticated molecular biological techniques. In addition, the method is suitable to simultaneously detect *M. tuberculosis* directly in clinical specimens and to type the micro-organisms, without the requirement to culture the slow-growing bacteria of the *M. tuberculosis* complex. Finally, in contrast to other methods of *M. tuberculosis* strain differentiation used sofar, the invention allows an easy and robust classification of different DNA types, without the need of sophisticated image processing software.

DETAILED DESCRIPTION OF THE INVENTION

The invention is based on the DNA polymorphism found at a unique chromosomal locus, the "Direct Repeat" (DR) region, which is uniquely present in *M. tuberculosis* complex bacteria. This locus was discovered by Hermans et al. (15) in *M. bovis* BCG, the strain used worldwide to vaccinate against tuberculosis. The DR region in *M. bovis* BCG consists of directly repeated sequences of 36 base pairs, which are interspersed by non-repetitive DNA spacers, each 35 to 41 base pairs in length (15). The number of copies of the DR sequence in *M. bovis* BCG was determined to be 49. In other strains of the *M. tuberculosis* complex the number of DR elements was found to vary (15). The vast majority of the *M. tuberculosis* strains contain one or more IS6110 elements in the DR containing region of the genome.

The recent study (12) described above showed that the genetic diversity in the DR region is generated by differences in the DR copy number, suggesting that homologeous recombination between DR sequences may be a major driving force for the DR-associated DNA polymorphism (12). The high degree of DNA polymorphism within a relatively small part of the chromosome makes this region well-suited for a PCR-based fingerprinting technique.

The invention described below is based on a unique method of in vitro amplification of DNA sequences within the DR region and the hybridisation of the amplified DNA with multiple, short synthetic oligomeric DNA sequences based on the sequences of the unique spacer DNA's within the DR region (FIG. 2). This differs from previous PCR methods in the use of a set of primers with both primers having multiple priming sites as opposed to having one of the primers bind to a fixed priming site such as to a part of IS6110. Because *M. tuberculosis* complex strains differ in the presence of these spacer sequences, strains can be differentiated by the different hybridisation patterns with a set of various spacer DNA sequences.

Determination of the DNA sequence of the complete DR region in *M. tuberculosis*.

FIG. 1 depicts the structure of the DR region of *M. bovis* BCG as determined previously by Hermans et al. and Groenen et al. (12, 15). For the sake of convenience we will designate a DR plus its 3' adjacent spacer sequence as a "Direct Variant Repeat" (DVR). Thus, the DR region is composed of a discrete number of DVR's, each consisting of a constant part (DR) and a variable part (the spacer).

The sequenced part of the DR region in *M. bovis* BCG is printed in black and it comprises 21 DVR's, 7 located 5' of the IS6110 element and 14 DVR's 3' of the IS6110 element (including the one in which the IS6110 element is located). The non-sequenced part is depicted in gray.

To determine the sequence of more spacers, we sequenced in this invention the sequence of the chromosomal region comprising the whole DR region of *M. tuberculosis* H37Rv and also sequences flanking the DR region. For this purpose we used cosmid T211 (obtained from Dr. Cole, Institut Pasteur, Paris), carrying the whole DR region. This cosmid contains an insert of about 35 kb from *M. tuberculosis* strain H37Rv. A physical map was constructed and the stretch containing the DR region was localized by Southern blotting. Subclones were prepared and the DNA flanking the IS6110 element residing in the DR cluster was sequenced. The sequence is given in FIG. 3 (SEQ ID NO: 1).

As shown schematically in FIG. 1, the number of DR's in strain H37Rv amounts to 41. As previously found in *M. bovis* BCG, again each DR was found to be interspersed by a unique spacer sequence, varying in size from 29 to 41 base pairs. the sequence of 13 DVR's of H37Rv are identical to 13 DVR's in the previously sequenced homologous chromosomal region of *M. bovis* BCG (15). The DVR's of H37Hv are numbered from 1 to 41. the numbering beginning from 5' terminal DVR. The identical DVR's are spacers 12 to 32.

The subject invention is directed at a method of in vitro amplification of nucleic acid using amplification primers in a manner known per se in amplification reactions such as PCR, LCR or NASBA, wherein a pair of primers is used comprising oligonucleotide sequences sufficiently complementary to a part of the Direct Repeat sequence of a microorganism belonging to the *M. tuberculosis* complex of microorganisms for hybridisation to a Direct Repeat to occur and subsequently elongation of the hybridized primer to take place, said primer being such that elongation in the amplification reaction occurs for one primer in the 5' direction and for the other primer in the 3' direction. Due to the multiple presence of Direct Repeats in the microorganisms to be detected the use of such primers implies that all the spacer regions will be amplified in an efficient manner. In particular it is not necessary for extremely long sequences to be produced in order to obtain amplification of spacers located at a distance from the primer. With the instant selection of the primer pairs a heterogenous product is obtained comprising a lot of smaller fragments all comprising spacer region nucleic acid. Subsequently the detection of the amplified product can occur simply by using an oligonucleotide probe directed at one or more of the spacer regions one wishes to detect. In order to avoid hindrance in the amplification reactions the primers can have oligonucleotide sequences complementary to non-overlapping parts of the Direct Repeat sequence so that when both primers hybridize to the same Direct Repeat and undergo elongation they will not be hindered by each other. In particular to avoid any hindrance during elongation reactions when one primer DRa is capable of elongation in the 5' direction and the other primer DRb is capable of elongation in the 3' direction the DRa is selected such that it is complementary to a sequence of the Direct Repeat located to the 5' side of the sequence of the Direct Repeat to which DRb is complementary. In a method according to the invention the primer used must have an oligonucleotide sequence capable of hybridising to the consensus sequence of the Direct Repeat in a manner sufficient for amplification to occur under the circumstances of the particular amplification reaction. A person skilled in the art of amplification reactions will have no difficulty in determining which length and which degree of homology is required for good amplification reactions to occur. The consensus sequence of the Direct Repeat of microorganisms belonging to the *M. tuberculosis* complex is given in FIG. 1. (SEQ ID NO: 2)

The invention is also directed at a method of detection of a microorganism belonging to the *M. tuberculosis* complex of microorganisms, comprising 1) amplifying nucleic acid from a sample with the method described above in any of the embodiments disclosed, followed by
2) carrying out a hybridisation test in a manner known per se, wherein the amplification product is hybridised to an oligonucleotide probe or a plurality of different oligonucleotide probes, each oligonucleotide probe being sufficiently homologous to a part of a spacer of the Direct Region of a microorganism belonging to the *M. tuberculosis* complex for hybridisation to occur to amplified product if such spacer nucleic acid was present in the sample prior to amplification, said hybridisation step optionally being carried out without prior electrophoresis or separation of the amplified product and
3) detecting any hybridised products in a manner known per se.

The detection method according to the invention can be carried out in a large number of embodiments which will depend on the objective of the detection method. For example, the method can be carried out by using a number of oligonucleotide probes in the hybridisation test, said number comprising at least a number of oligonucleotide probes specific for the total spectrum of microorganisms it is desired to detect. For example, one can use oligonucleotide probes of spacer regions known to be present in all microorganisms belonging to the *M. tuberculosis* complex. Use of one such oligonucleotide probe will suffice to detect whether infection with a *M. tuberculosis* microorganism has occurred. It is also possible to use a combination of oligonucleotide probes specific for certain types of *M. tuberculosis* complex microorganisms. For example, 13 spacer regions of the strain *M. tuberculosis* H37Rv have been found to be shared with *M. bovis* BCG. However, a large number of spacers from both types of microorganisms differ. It is therefore possible to select specific combinations of oligonucleotide probes in order to differentiate between the various strains. As the majority of tuberculosis infections are due to infections with microorganisms from the groups *M. tuberculosis*, *M. bovis* and *M. africanum* a method for detection of a microorganism according to the invention will preferably be directed at detection of the presence of such microorganisms. The spacer sequences of *M. tuberculosis* H37Rv and the spacer sequence of the *M. bovis* BCG have been determined. *M. tuberculosis* H37Rv comprises 41 spacer sequences and the sequences are given elsewhere in the text as sequence id. nos. 3 to 43 *M. bovis* BCG spacer sequences are described in (15) by Hermans et al. In FIG. 2 of the cited reference Direct Repeats 24–43 are disclosed for *M. bovis* BCG strain 44 containing IS987. The intermediate spacer region sequences are also provided in this figure. The sequence data of the cited reference have appeared in the EMBL Genbank and DDBJ Nucleotide Sequence Databases under the accession number X57835. The spacer regions that have been found to be common for *M. tuberculosis* H37Rv and *M. bovis* BCG are the spacers 20 to 32 of *M. tuberculosis* H37Rv.

A method according to the invention as disclosed in any of the embodiments above can be carried out using an oligonucleotide probe being a sequence complementary to any of the spacer sequences of *M. tuberculosis* H37Rv or any of the spacer sequences of *M. bovis* BCG or a sequence complementary to fragments or derivatives of said spacer sequences, said oligonucleotide probe being capable of hybridising to such a spacer sequence and comprising at least seven consecutive nucleotides homologous to such a spacer sequence and/or exhibiting at least 60% homology, preferably exhibiting at least 80% homology with such a spacer sequence and being at least 7 nucleotides long. In particular if one wishes to detect the presence of either *M. tuberculosis* H37Rv or *M. bovis* BCG any of the common spacer sequences can be used for providing a suitable oligonucleotide probe for a method according to the invention.

The invention is also directed at a method for differentiating the type of microorganism belonging to the *M. tuberculosis* complex in a sample, in particular at a method wherein the sample is a clinical specimen. The method can be carried out on a sample without the cells from the sample having to be cultured for analysis to be carried out. Such a method comprises carrying out the detection method according to the invention as disclosed above, followed by comparison of the hybridisation pattern obtained with a reference. The reference can be the hybridisation pattern obtained with one or more strains of microorganism belonging to the *M. tuberculosis* complex of microorganisms in an analogous manner to that of the sample. Another possibility is to examine the result wherein the reference is a source providing a list of spacer sequences and sources thereof, such as a data bank. Through predetermined analysis of such a data bank and specific selection of oligonucleotide probes a differentiating test can be provided specifically suited to the microorganism strain or strains one wishes to differentiate between. In the example illustrating the invention 77 clinical samples were analysed using a large number of oligonucleotide probes and an illustration of the types of hybridisation patterns that can be expected with a method according to the invention is given. Due to the specific nature of the spacer regions and the specific combination of spacer regions in various strains these spacer regions are especially suited for differentiating tests. This is why such spacer sequences from the template for designing oligonucleotide probes, suitable in a detection method or differentiating method according to the invention. The invention is therefore also directed at oligonucleotide probes of at least 7 nucleotides, preferably more than 12 nucleotides, in particular comprising between 12 to 40 nucleotides, said probe being sufficiently homologous to any of the following spacer sequences; spacer sequences 1–23 of *M. bovis* BCG, spacer sequences 44–49 of *M. bovis* BCG and spacer regions 1–43 of *M. tuberculosis* H37Rv with the exception of the *M. tuberculosis* H37Rv sequences common to *M. bovis* BCG. i.e. with the exception of any spacer regions corresponding to numbers 20–32 of *M. bovis* BCG. In particular Sequence id. No's 3–21 and 35–43 fall within the scope of the invention. The invention is also directed at fragments or derivatives of such spacer sequences capable of hybridising to such a spacer sequence, said oligonucleotide probe being at least 7 oligonucleotides long, preferably more than 12 nucleotides, in particular comprising between 12 to 40 nucleotides and comprising at least 7 consecutive nucleotides homologous to such a spacer sequence and/or exhibiting at least 60% homology, preferably exhibiting at least 80% homology, most preferably exhibiting more than 90% homology with the corresponding part of the spacer sequence.

The invention is also directed at a carrier comprising oligonucleotide probes comprising at least one oligonucleotide probe wherein the oligonucleotide probe is specific for a spacer region of a microorganism of the group belonging to *M. tuberculosis* complex. In particular at a carrier comprising an oligonucleotide probe according to the invention as disclosed above.

The invention is also directed at a pair of primers wherein both primers comprise oligonucleotide sequences sufficiently complementary to a part of the Direct Repeat sequence of a microorganism belonging to the *M. tuberculosis* complex of microorganisms for hybridisation to occur and subsequently elongation of the hybridised primer to take place, said primers being such that elongation in the amplification reaction occurs for one primer in the 5' direction and for the other primer in the 3' direction and wherein sufficiently complementary means said oligonucleotide sequence comprises at least seven consecutive nucleotide homologous to such a Direct Repeat sequence, in particular the consensus sequence of a Direct Repeat (sequence id. no. 2) and/or exhibits at least 60% homology, preferably exhibits at least 80% homology, most preferably exhibits more than 90% homology with the corresponding part of the direct repeat sequence and is at least 7 oligonucleotides long. In particular the primer pair DRa and DRb described in the example are a primer pair suitable for carrying out the invention. A primer pair as disclosed comprising one primer DRa capable of elongation in the 5' direction and the other primer DRb capable of elongation in the 3' direction with DRa being complementary to a sequence of the Direct Repeat located to the 5" side of the sequence of the Direct Repeat to which DRb is complementary, the Direct Repeat being present in the Direct Region of a microorganism belonging to the group of *M. tuberculosis* complex falls within the scope of the invention.

A kit for carrying out a method for in vitro amplification of nucleic acid using amplification primers in a manner known per se in amplification reactions such as PCR, LCR or NASBA wherein a pair of primers is used comprising oligonucleotide sequences sufficiently complementary to a part of the Direct Repeat sequence of a microorganism belonging to the *M. tuberculosis* complex of microorganisms for hybridisation to a Direct Repeat to occur and subsequently elongation of the hybridised primer to take place, said primers being such that elongation in the amplification reaction occurs for one primer in the 5' direction and for the other primer in the 3' direction is an embodiment of the invention. Such a kit must comprise a suitable primer pair as disclosed according to the invention. The kit of the invention can also be suitable for carrying out a method of detection of a microorganism belonging to the *M. tuberculosis* complex of microorganisms as described. Such a kit comprises a primer pair as disclosed for the amplification method and an oligonucleotide sequence as disclosed being sufficiently homologous to a spacer sequence of a Direct Region of a microorganism belonging to the *M. tuberculosis* complex or a carrier comprising such an oligonucleotide sequence in any of the embodiment disclosed in the description for detection and differentiation.

EXAMPLE

In vitro amplification of the DR-containing region in clinical isolates of *M. tuberculosis*.

The chromosomal DR region of 74 different clinical isolates of *M. tuberculosis* was amplified by the polymerase chain reaction (PCR), using the primer pair DRa (with Sequence id. no. 50) and DRb (with Sequence id. no. 51). As illustrated in FIG. 4, a reaction product was obtained from all strains investigated and the amplified DNA was heterogenous in size. This heterogeneity is to be expected, because the primers DRa and DRb can initiate the PCR at any of the DVR's in the DR region. Therefore each of the DVR's is expected to be present in the amplified PCR product. A good amplification is obtained in particular for the spacer regions at the termini of the direct region in contrast to the known PCR amplification reaction using nucleic acid of the IS fragment as primer (15 and 34).

Hybridisation of the amplified DR region to individual spacer sequences of H37Rv.

The PCR products of the 74 above-mentioned strains were hybridized to 47 spacer sequences, which were covalently bound to Biodyne C paper as described (18). Because the PCR products contained a biotin label, which was incorporated during the PCR, hybridizing DNA could be visualized by binding of a strepavidin-containing peroxidase conjugate and an enzyme assay. The result is shown in FIG. 5. DVR-amplified DNA of all strains hybridized with at least 9 of the 47 oligonucleotides. Depending on the combination of spacer oligonucleotides hybridizing with the PCR-amplified DNA, 39 different "DVR types" of *M. tuberculosis* were distinguished. This experiment shows that any *M. tuberculosis* strain can be typed by this method, without the need to separate amplified *M. tuberculosis* DNA by electrophoresis. The 74 strains were also typed by the classical IS6110 fingerprinting method as described (32) and 66 different IS6110 types were distinguished. This indicates that the level of strain differentiation using IS6110 fingerprinting is slightly higher compared to the method described in this invention. This method will be referred to as "DVR-oligotyping". The method of DVR-oligotyping is however sufficiently specific to discern a large number of strains within a group such as *M. bovis* BCG and *M. tuberculosis* H37Rv and H37Ra.

Specificity of the DVR oligotyping method.

To determine whether the method of amplification and hybridisation is specific for bacteria belonging to the *M. tuberculosis* complex, we subjected 40 DNA samples originating from a wide variety of mycobacterial species and other bacterial genera to the DVR oligotyping method. The target DNA's included the following bacterial species: *E. coli, Bordetella pertassis, Afipia felis, Rochalimea lenselae, Mycobacterium avium*. None of these targets led to a detectable positive hybridization reaction with any of the spacer oligonucleotides, hereby illustrating the specificity of the subject method.

Detection of *M. tuberculosis* in clinical specimens by DVR-oligotyping.

The sensitivity to detect *M. tuberculosis* by the above described method was tested by carrying out DVR-oligotyping with various amounts of chromosomal DNA of strains H37Rv. *M. bovis* BCG and 2 clinical isolates of *M. tuberculosis*. The sensitivity to detect DNA from each of these strains was at least 64 femtogram (fg) of DNA. 1 fg of chromosomal DNA corresponds approximately to the quantity present in a single bacterium and it is assumed, the DVR-oligotyping method will allow the simultaneous detection and typing of DNA derived from a single bacterium.

Furthermore, clinical sputa samples obtained from Dr. A. Kolk (Royal Tropical Institute, Amsterdam) were subjected to DVR-oligotyping, i.e. to the detection and differentiation methods according to the invention. All culture-positive samples were positive by DVR-oligotyping and the DVR type corresponded to the type as determined from purified DNA extracted from *M. tuberculosis* cultured from the corresponding sputum samples.

MATERIALS AND METHODS

Determination of the DNA sequence of the DR region in H37Rv.

Cosmid T211, which contains a 35 Kb insert carrying the complete DR region of strain H37Rv, was obtained from Dr S. Cole (Institut Pasteur, Paris). A physical map of cosmid T211 is shown in FIG. 6. MluI fragments of this cosmid were subcloned into MluI-cleaved DNA of plasmid pUCBM21. resulting in plasmids pPG11, pPG17 and pPG33 (FIG. 6). The latter 3 plasmids were used to sequence the complete DR containing region of strain H37Rv. Sequencing was performed according to the dideoxy chain termination method of Sanger et al. (28), using a 373A DNA Sequencer (Applied Biosystems, Fosre City, Calif. USA) following the protocols provided by the manufacturer).

Extraction of DNA from mycobacterial cells.

DNA was purified as described previously (33).

Bacterial strains used in this study.

*Escherichia coli* K12 strain DH5α (BRL, Maryland, USA) was used as a host for propagating plasmid pUCBM21 and derivatives. *M. bovis* BCG strain P3 and *M. tuberculosis* H37Rv have been described previously (12, 15). All other bacterial strains were clinical isolates, which were sent to the RIVM.

DVR oligotyping.

In vitro amplification of DNA.

10 Nanogram of purified *M. tuberculosis* DNA was added to a mixture containing 0.5 unit Super Tth polymerase (HT Biotechnology, Cambridge, UK). 5 µl of 10× concentrated Super Rth buffer (HT biotechnology, Cambridge, UK), 20 nMol of each dNTP, and 20 pMol of each of the primers DRa and DRb. The final volume was adjusted to 50 µl. this mixture was subjected to 30 cycles of amplification using the following scheme: 1 min. 96° C. 1 min. 55° C. and 30 sec. 72° C.

Reverse line blot hybridization.

Oligonucleotides with a 5' terminal amino group were linked covalently to activated Biodyne C membrane (18, 38). The Biodyne C membrane (Pall Biosupport, Glen Cove, N.Y., USA) was activated by incubation for 10 min. in 10 ml freshly prepared 16% (w/v) 1- ethyl-3-(3-dimethylaminopropyl)carbodiimide. The blot was rinsed with water and placed immediately in a miniblotter system (Immunetics, ITK Diagnostics, Uithoorn, The Netherlands). Each slot of the miniblotter was filled with 150 µl of a 0.125 µM oligonucleotide solution in 500 mM $NaHCO_3$, pH 8.4. After 1 min. incubation at room temperature, the oligonucleotide solutions were removed by aspiration. The filter was removed from the miniblotter, treated with 100 mM NaOH for 10 min. to inactivate the membrane and washed in 2×SSPE (360 mM NaCl, 20 mM $NaH_2PO_4$, 2 mM EDTA, pH 7.2). supplemented with SDS (0.1%) for 5 min. at 54° C. The filter was mounted into the miniblotter, in such a way that the slots were perpendicular to the line pattern of the applied oligonucleotides. The slots of the miniblotter were filled with 150 µl of diluted, heat-denatured, biotin-labeled PCR products (20 µl PCR product diluted in 130 µl 2×SSPE, 0.1% SDS) and hybridized for 45 min at 54° C. after emptying the slots by aspiration, the filter was washed in 150 ml of 2×SSPE, 0.5% SDS for 10 min. at 54° C. and incubated in 10 ml of streptavidin-peroxidase conjugate (Boehringer, Mannheim) diluted 1:4000 in 2×SSPE. (0.5% SDS) for 30 min. at 42° C. The filter was washed in 150 ml of 2×SSPE, 0.5% SDS for 10 min. at 42° C. and rinsed briefly at room temperature with 150 ml of 2×SSPE. For chemiluminescent detection of hybridizing DNA the filter was incubated in 10 ml ECL detection liquid (Amersham, 's Hertogenbosch, The Netherlands) and exposed for one min. to X-ray film (Hyperfilm, Amersham).

BRIEF DESCRIPTION OF THE DRAWINGS

Legend to FIG. 1.

Structure of the DR region of *M. bovis* BCG and *M. tuberculosis* H37Rv. The rectangles depict the 36 bp DR sequences, which are interspersed by unique spacers varying 29 to 41 bp in size. The site of insertion of the IS6110 element in the DR region is depicted. Part of the DR region of *M. bovis* BCG has been sequenced previously (15) and this part is depicted in black. The non-sequenced part is in gray. The whole DR region of H37Rv was sequenced as part of the invention. Gaps in the H37Rv sequence indicate the absence of DVR's, which are present in *M. bovis* BCG.

Legend to FIG. 2.

Principle of the in vitro amplification of DNA within the DR region of *M. tuberculosis* complex bacteria. The repeating units within the DR cluster are the DVR's. Each DVR is composed of a constant 36 base pair sequence, DR, and a variable part, the spacer (A, B, C and D, respectively). Four sequential DVR's are represented as DVR-A, DVR-B, DVR-C, and DVR-D. The use of the 2 primers, DRa and DRb (arrows a and b), having sequences based on the DR sequence, for in vitro amplification of DNA, will lead to the amplification of any DVR or a stretch composed of a discrete number of neighbouring DVR's.

Legend to FIG. 3.

Nucleotide sequence of the DR region in *M. tuberculosis* strain H37Rv and the regions flanking the DR region. Sequences homologous to the DR sequence are underlined, sequences used as oligonucleotides in the assay are printed in bold.

Figure 1:
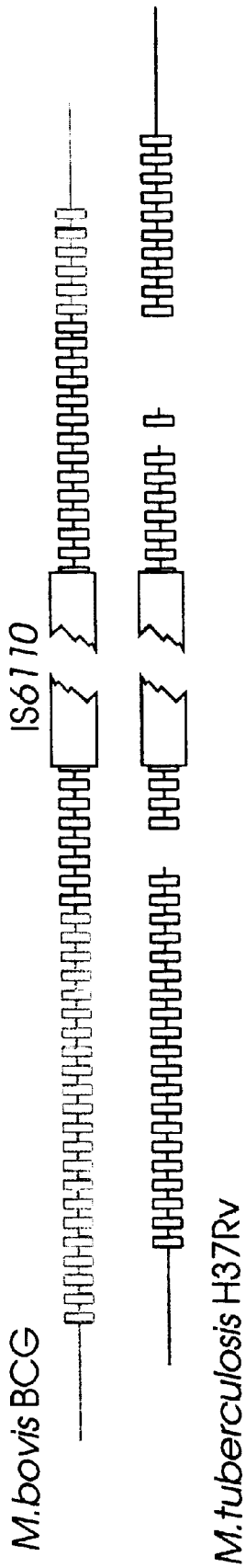
Figure 4:
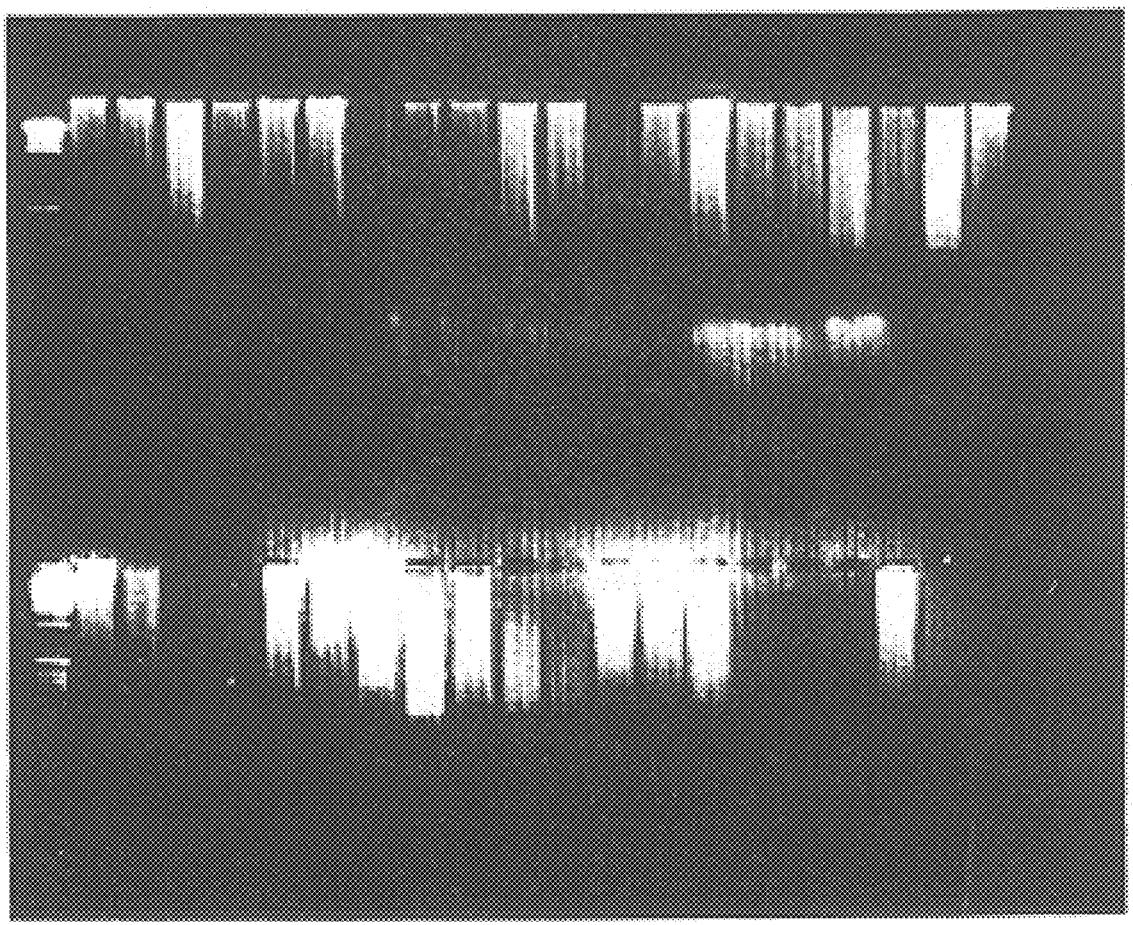

Legend to FIG. 4.

Gel electrophoresis of in vitro amplified *M. tuberculosis* DNA amplified by PCR using the primers DRa and DRb. Each lane was loaded with one-fifth of the total amount of amplified DNA from different clinical *M. tuberculosis* isolates. The quantity of DNA used as a target for the PCR was 10 nanogram.

Figure 5:
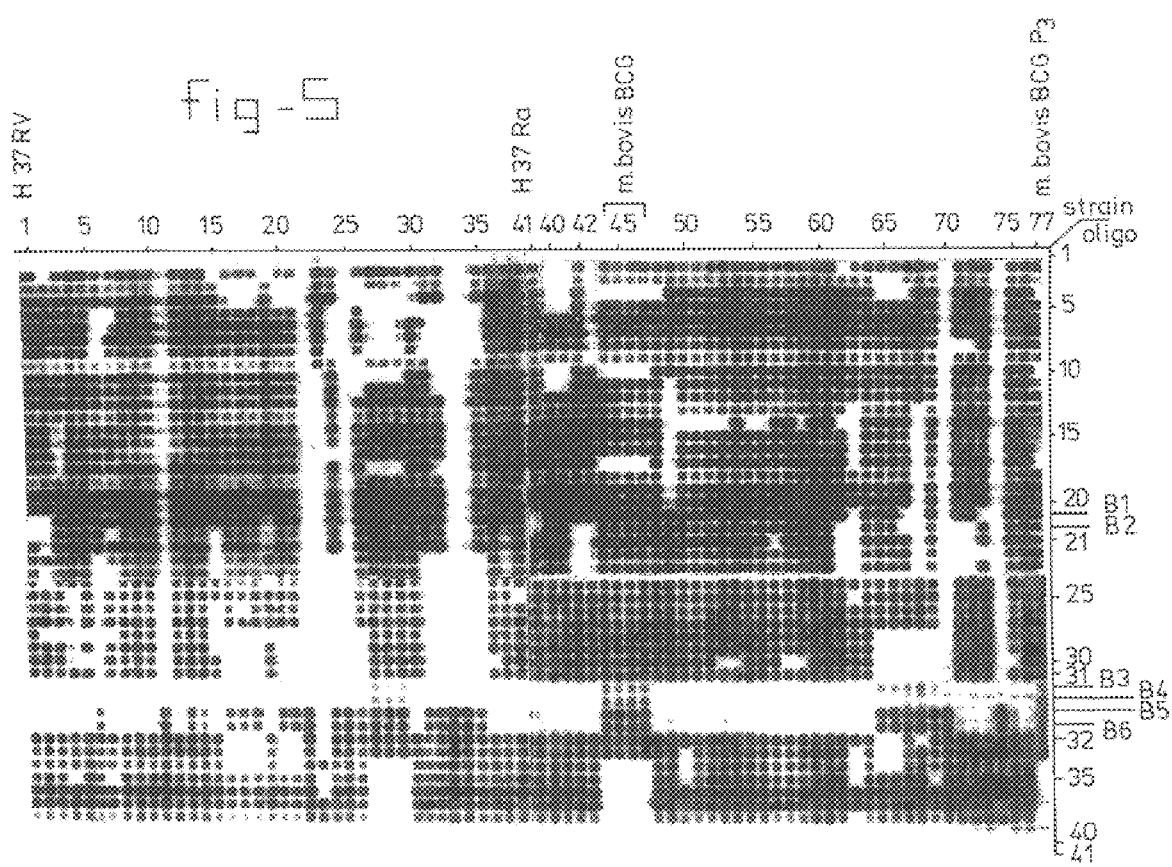

Legend to FIG. 5.

Hybridisation patterns of the in vitro amplified DVR products of 72 different *M. tuberculosis* isolates and 5 different *M. bovis* BCG isolates with 41 different oligonucleotides. The oligonucleotides used are derived from the spacer sequences 1 to 41 as described in Materials and Methods. The primers Dra and Drb (see FIG. 2) were used as drivers for the in vitro amplification of the DVR's with the DR region.

The spacer oligonucleotides were covalently bound to a Biodyne C filter in a pattern of parallel lines and the hybridization with in vitro amplified DVR DNA was done in parallel channels perpendicular to the spacer oligonucleotide pattern as described in the materials and methods. Strain 1: H37Rv; strain 41: H37Ra; strains 44–46: different *M. bovis* BCG isolates; strain 77: *M. bovis* BCG P3; all other strains: clinical isolates of *M. tuberculosis*.

Figure 6:
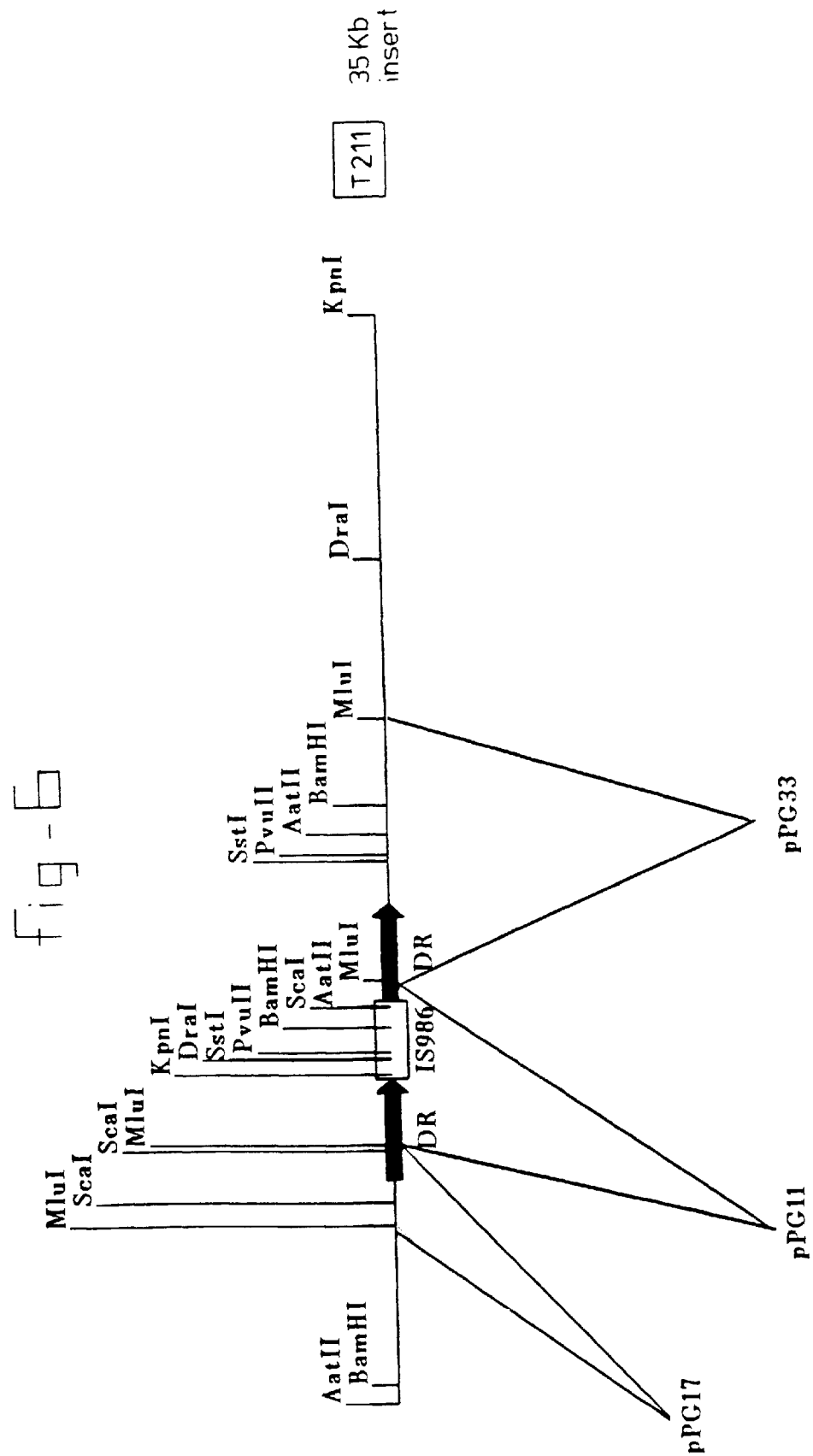

Legend to FIG. 6.

Restriction map of the insert of cosmid T211, containing the complete DR region of H37Rv; localisation of the MluI fragments subcloned into the plasmids pPG17, pPG11, and pPG33.

REFERENCES

1. Beck-Sagué, C., S. W. Dooley, M. D. Hutton. J. Otten, A. Breeden, J. T. Crawford, A. E. Pitchenik, C. Woodley, G. Cauthen, W. R. Jarvis. 1992 Hospital outbreak of multidrug-resistant *Mycobacterium tuberculosis* infections. JAMA. 268: 1280–1286.

2. Brudney. K., Dobkin J. 1991. Resurgent tuberculosis in New York City: Human immunodeficiency virus, homelessness, and the decline of tuberculosis control programs. Am. Rev. Resp. Dis. 144: 745–749.

3. CDC. 1992. Transmission of multidrug-resistant tuberculosis among immunocompromised persons in a correctional system. New York 1991. MMWR 41: 507–509.

4. CDC. 1991. Nosoconial transmission of multidrug resistant tuberculosis among HIV-infected persons. Florida and New York, 1988–1991. MMWR 40: 585–591.

5. Cave, M. D., K. D. Eisenach, P. F. McDermott, J. H. Bates, and J. T. Crawford. 1991. IS6110: Conservation of sequence in the *Mycobacterium tuberculosis* complex and its utilization in DNA fingerprinting. Mol. Cell. Probes 5:73–80.

6. Daley, C. L. P. M. Small. G. F. Schecter, G. K. Schoolnik. R. A. McAdam, W. R. Jacobs, Jr., and P. C. Hopewell. 1992. An outbreak of tuberculosis with accelerated progression among persons infected with the human immunodeficiency virus: an analysis using restriction fragment length polymorphisms. N. Engl. J. Med. 326:231–235.

7. Dooley, S. W., M. E. Villarino, M. Lawrence, et al. 1992. Nosocomial transmission of tuberculosis in a hospital unit for HIV-infected patients. JAMA. 267:2632–2634.

8. Dwyer, B., K. Jackson, K. Raios. A. Sievers, E. Wilshire and B. Ross. 1993. DNA Restriction fragment analysis to define an extended cluster of tuberculosis in homeless men and their associates. J. Inf. Diseases, 167: 490–494.

9. Edlin, B. R., J. I. Tokars, M. H. Grieco, J. T. Crawford, J. Williams, E. M. Sordillo, K. R. Ong, J. O. Kilburn, S. W. Dooley, K. G. Castro, W. R. Jarvis and S. D, Holmberg. 1992. An outbreak of multidrug-resistent tuberculosis among hospitalized patients with the acquired immunodeficiency syndrome. N. Eng. J. Med. 326:1514–1521.

10. Fischl, M. A, R. B. Uttamchandani, G. L. Daikos, et al. 1992. An outbreak of tuberculosis caused by multiple-drug resistant tubercle bacilli among patients with HIV infection. Ann. Intern. Med. 117:177–183.

11. Fomukong, N. G., J. W. Dale, T. W. Osborn and J. M. Grange. 1992. Use of gene probes on the insertion sequence IS986 to differentiate between BCG vaccine strains. J. Appl. Bacteriol. 72:125–133.

12. Groenen, P. M. A., A. E. van Bunschoten, D. van Soolingen, and J. D. A. van Embden. 1993. Nature of DNA polymorphism in the direct repeat cluster of *Mycobacterium tuberculosis*; Application for strain differentiation by a novel method. Mol. Microbiol. (1993) 10 (5) 1057–1065.

13. Haas, W. H., W. R. Butler, Ch. L. Woodley and J. T. Crawford. 1993. Mixed-linker polymerase chain reaction: a new method for rapid fingerprinting of isolates of the *Mycobacterium tuberculosis* Complex. J. Clin. Microbiol. 31:1293–1298.

14. Hermans, P. W. M., D. van Soolingen. J. W. Dale, A. R. Schuitema, R. A. McAdam, D. Catty, and J. D. A. van Embden. 1990. Insertion element IS986 from *Mycobacterium tuberculosis*: a useful tool for diagnosis and epidemiology of tuberculosis. J. Clin. Microbiol. 28:2051–2058.

15. Hermans, P. W. M., D. van Soolingen. E. M. Bik, P. E. W. de Haas, J. W. Dale, and J. D. A. van Embden. 1991. The insertion element IS987 from *M. bovis* BCG is located in a hot spot integration region for insertion elements in *M. tuberculosis* complex strains. Infect. Immun. 59:2695–2705.

16. Hermans, P. W. M., D. van Soolingen, and J. D. A. van Embden. 1992. Characterization of a major polymorphic tandem repeat in *Mycobacterium tuberculosis* and its potential use in the epidemiology of *Mycobacterium kansasii* and *Micobacterium gordonae*. J. Bacteriol. 174:4157–4165.

17. Jeffreys, A. J., A. Macleod, K. Tamaki, D. L. Neil and D. G. Monckton. 1991. Minisatellite repeat coding as a digital approach to DNA typing. 354: 204–209.

18. Kaufholt, A., A. Podbielski, G. Baumgarten, M. Blokspoel, J. Top, and L. Schouls. 1994. Rapid typing of group A streptococci by the use of DNA amplification and non-radioactive allele specific oligonucleotide probes. FEMS Microbiology Letters, in press.

19. Mazurek, G. H., M. D. Cave, K. D. Eisenach, R. J. Wallace JR, J. H. Bates, and J. T. Crawford. 1991. Chromosomal DNA fingerprint patterns produced with IS6110 as strain specific markers for epidemiologic study of tuberculosis. J. Clin. Microbiol. 29:2030–2033.

20. McAdam, R. A., P. W. M. Hermans, D. van Soolingen, Z. F. Zainuddin, D. Catty. J. D. A. van Embden, and J. W. Dale. 1990. Characterization of a *Mycobacterium tuberculosis* insertion sequence belonging to the IS3 family. Mol. Microbiol. 4:1607–1613.

21. Mendiola, M. V., C.. Martin, I. Otal, and B. Gicquel. 1992. Analysis of regions responsible for IS6110 RFLP in a single *Mycobacterium tuberculosis* strain. Res. Microbiol. 143:767–772.

22. Otal, I., C. Martin, V. Vincent-Lévy-Frébault. D. Thierry, and B. Gicquel. 1991. Restriction fragment length polymorphism analysis using IS6110 as an epidemiological marker in tuberculosis. J. Clin. Microbiol. 29:1252–1254.

23. Palittapongarnpim. P., S. Chomic, A. Fanning, and D. Kunimoto. 1993. DNA fingerprinting of *Mycobacterium tuberculosis* by ligation-mediated polymerase chain reaction. Nucl. Ac. Res. 3:761–762.

24. Palittapongarnpim. P., S. Chomic, A. Fanning. and D. Kunimoto. 1993. DNA fragment length polymorphism analysis of *M. tuberculosis* isolating by arbitrarily primed polymerase chain reaction. J. Inf. Diseases 167:975–978.

25. Palittapongarnpim, P. S., S. Rienthong, and W. Panbangred. 1993. Comparison of restriction fragment length polymorphism of *M. tuberculosis* isolated from cerebrospinal fluid and sputum: a preliminary report. Tubercle and lung disease 1993. 74, 204–207.

26. Ross, C., K. Raios. K. Jackson, and B. Dwyer. 1992. Molecular cloning of a hightly repeated element from *Mycobacterium tuberculosis* and its use as an epidemiological tool. J. Clin. Microbiol. 30:942–946.

27. Ross, B. C., and B. Dwyer. 1993. Rapid, simple method for typing isolates of *Mycobacterium tuberculosis* by using the polymerase chain reaction. J. Clin. Microbiol. 31:329–334.

28. Sanger, F., Nicklen, S. and Coulson, A. R. (1977) DNA Sequencing with chain-termination inhibitors. Proc. Natl. Acad. Sci. U.S.A. 74:5463–5467.

29. Small. P. M., R. W. Schafer. P. C. Hopewell, S. P. Singh, M. J. Murphy, E. Desmond. M. F. Sierra, and G. K. Schoolnik. 1993. Exogenous reinfection with multidrug-resistant *M. tuberculosis* in patients with advanced HIV infection. N. Eng. J. Med. 328:1137–1144.

30. Thierry, D., M. D. Cave, K. D. Eisenach, J. T. Crawford, J. H. Bates. B. Gecquel. and J. L. Guesdon. 1990. IS610. an IS-like element of *M. tuberculosis* complex. Nucleic Acids Res. 18:188.

31. Van Embden, J. D. A., D. van Soolingen, P. M. Small, and P. W. M. Hermans. 1992. Genetic markers for the epidemiology of tuberculosis. Res. Microbiol. 143: 385–391.

32. Van Embden, J. D. A., M. D. Cave, J. T. Crawford, J. W. Dale, K. D. Eisenach, B. Gicquel, P. W. M. Hermans, C. Martin, R. McAdam, T. M. Shinnick, and P. M. Small. 1993. Strain identification of *Mycobacterium tuberculosis* by DNA fingerprinting; Recommendations for a standardized Methodology J. Clin. Microbiol. 31:406–409.

33. Van Soolingen, D., P. W. M. Hermans, P. E. W. de Haas, D. R. Soll, and J. D. A. van Embden. 1991. The occurrence and stability of insertion sequences in *Mycobacterium tuberculosis* complex strains; evaluation of IS-dependent DNA polymorphism as a tool in the epidemiology of tuberculosis. J. Clin. Microbiol. 29:2578–2586.

34. Van Soolingen, D., P. W. M. Hermans, P. E. W. de Haas, and J. D. A. van Embden. 1992. Insertion element IS1081-associated Restriction Fragment Length Polymorphism in *Mycobacterium tuberculosis* Complex spacies: a reliable tool for recognizing *Mycobacterium bovis* BCG. J. Clin. Microbiol. 30:1772–1777.

35. Van Soolingen, D., P. E. W. de Haas, P. W. M. Hermans, P. M. A. Groenen and J. D. A. van Embden. 1993. Comparison of various repetitive DNA elements as genetic markers for strain differentiation and epidemiology of *Mycobacterium tuberculosis*. J. Clin. Microbiol. 31:1987–1995.

36. Yuen L. K., B. C. Ross, K. M. Jackson, and B. Dwyer. 1992. Characterization of *Mycobacterium tuberculosis* strains from Vietnamese patients by southern blot hybridization. J. Clin. Micro. 31: 1615–1618.

37. WHO. 1993. Tuberculosis in the present time: A global overview of the tuberculosis situation. Tuberculosis Unit, Division of Communicable Diseases. Geneva.

38. Y. Zhang, M. Y. Coyne, S. G. Will, C. H. Levenson, and E. Kawasaki. 1991. Single-base mutational analysis of cancer and genetic diseases using membrane bound modified oligonucleotides. Nucl. Acids Res. 19:3929–3933. Oligonucleotides used for DVR oligotyping referring to in the Sequence Listing

| Spacer No.: | Sequence id. No.: | |
|---|---|---|
| 01 | 3 | 5' TTG TAC TGC AAC CCG GAA TTC TTG A 3' |
| 02 | 4 | 5' ATA GAG GGT CGC CGG TTC TGG ATC A 3' |
| 03 | 5 | 5' CCT CAT AAT TGG GCG ACA GCT TTT G 3' |
| 04 | 6 | 5' CCG TGC TTC CAG TGA TCG CCT TCT A 3' |
| 05 | 7 | 5' ACG TCA TAC GCC GAC CAA TCA TCA G 3' |
| 06 | 8 | 5' TTT TCT GAC CAC TTG TGC GGG ATT A 3' |
| 07 | 9 | 5' CGT CGT CAT TTC CGG CTT CAA TTT C 3' |

-continued

| Spacer No.: | Sequence id. No.: | |
|---|---|---|
| 08 | 10 | 5' GAG GAG AGC GAG TAC TCG GGG CTG C 3' |
| 09 | 11 | 5' CGT GAA ACC GCC CCC AGC CTC GCC G 3' |
| 10 | 12 | 5' ACT CGG AAT CCC ATG TGC TGA CAG C 3' |
| 11 | 13 | 5' TCG ACA CCC GCT CTA GTT GAC TTC C 3' |
| 12 | 14 | 5' GTG AGC AAC GGC GGC GGC AAC CTG G 3' |
| 13 | 15 | 5' ATA TCT GCT GCC CGC CCG GGG AGA T 3' |
| 14 | 16 | 5' GAC CAT CAT TGC CAT TCC CTC TCC C 3' |
| 15 | 17 | 5' GGT GTG ATG CGG ATG GTC GGC TCG G 3' |
| 16 | 18 | 5' CTT GAA TAA CGC GCA GTG AAT TTC G 3' |
| 17 | 19 | 5' CGA GTT CCC GTC AGC GTC GTA AAT C 3' |
| 18 | 20 | 5' GCG CCG GCC CGC GCG GAT GAC TCC G 3' |
| 19 | 21 | 5' CAT GGA CCC GGG CGA GCT GCA GAT G 3' |
| 20 | 22 | 5' TAA CTG GCT TGG CGC TGA TCC TGG T 3' |
| 21 | 23 | 5' ACC GCA GAC GGC ACG ATT GAG ACA A 3' |
| 22 | 24 | 5' AGC ATC GCT GAT GCG GTC CAG CTC G 3' |
| 23 | 25 | 5' CCG CCT GCT GGG TGA GAC GTG CTC G 3' |
| 24 | 26 | 5' GAT CAG CGA CCA CCG CAC CCT GTC A 3' |
| 25 | 27 | 5' CTT CAG CAC CAC CAT CAT CCG GCG C 3' |
| 26 | 28 | 5' GGA TTC GTG ATC TCT TCC CGC GGA T 3' |
| 27 | 29 | 5' TGC CCC GGC GTT TAG CGA TCA CAA C 3' |
| 28 | 30 | 5' AAA TAC AGG CTC CAC GAC ACG ACC A 3' |
| 29 | 31 | 5' GGT TGC CCC GCG CCC TTT TCC AGC C 3' |
| 30 | 32 | 5' TCA GAC AGG TTC GCG TCG ATC AAG T 3' |
| 31 | 33 | 5' GAC CAA ATA GGT ATC GGC GTG TTC A 3' |
| 32 | 34 | 5' CGC GAA CTC GTC CAC AGT CCC CCT T 3' |
| 33 | 35 | 5' CGT GGA TGG CGG ATG CGT TGT GCC C 3' |
| 34 | 36 | 5' GAC GAT GGC CAG TAA ATC GGC GTG G 3' |
| 35 | 37 | 5' CGC CAT CTG TGC CTC ATA CAG GTC C 3' |
| 36 | 38 | 5' GGA GCT TTC CGG CTT CTA TCA GGT A 3' |
| 37 | 39 | 5' ATG GTG GGA CAT GGA CGA GCG CGA C 3' |
| 38 | 40 | 5' CGC AGA ATC GCA CCG GGT GCG GGA G 3' |
| 39 | 41 | 5' ATA TCG CCC GCC ACA CCA CAG CCA C 3' |
| 40 | 42 | 5' CGC CGA TGA CAG CTA TGT CCG AGT G 3' |
| 41 | 43 | 5' TTC GCG CGG TGT TTC GGC CGT GCC C 3' |
| B1 | 44 | 5' TTG ACC TCG CCA GGA GAG AAG ATC A 3' |
| B2 | 45 | 5' TCG ATG TCG ATG TCC CAA TCG TCG A 3' |
| B3 | 46 | 5' GAC ATG ACG GCG GTG CCG CAC TTG A 3' |
| B4 | 47 | 5' AAG TCA CCT CGC CCA CAC CGT CGA A 3' |

-continued

| Spacer No.: | Sequence id. No.: | |
|---|---|---|
| B5 | 48 | 5' TCC GTA CGC TCG AAA CGC TTC CAA C 3' |
| B6 | 49 | 5' CGA AAT CCA GCA CCA CAT CCG CAG C 3' |
| DRa | 50 | 5' CCG AGA GGG GAC GGA AAC 3' |
| DRb | 51 | 5' GGT TTT GGG TCT GAC GAC 3' |

All oligonucleotide sequences are derived from sequences or the DR region in strain *M. tuberculosis* H37Rv, except for oligonucleotides which are printed in bold. Latter ones are derived from the *M. bovis* BCG sequence (15). The 5' termini or the spacer oligonucleotides were linked to an amino-group in order to enable a covalent binding to the Biodyne C Membranes. All oligonucleotides were obtained from Applied Biosystems Incorporated, Perkin Elmer B. V., Gouda, The Netherlands.

What is claimed is:

1. In a method of in vitro amplification of nucleic acid using amplification primers in amplification reactions, the improvement comprising using a pair of primers comprising oligonucleotide sequences complementary to a part of a Direct Repeat sequence of a microorganism belonging to the *M tuberculosis* complex of microorganisms, whereby hybridization to a Direct Repeat occurs and subsequently elongation of the hybridized primer takes place, said primers being such that elongation in the amplification reaction occurs for one primer in a 5' direction and for the other primer in a 3' direction.

2. A method according to claim 1, wherein said primers have oligonucleotide sequences complementary to non-overlapping parts of the Direct Repeat sequence and such that the elongation reactions from each primer can occur without hindrance of the other when both primers hybridize to the same Direct Repeat and undergo elongation.

3. A method according to claim 1, wherein one primer DRa is capable of elongation in the 5' direction and another primer DRb is capable of elongation in the 3' direction and DRa is complementary to a sequence of the Direct Repeat located to the 5' side of the sequence of the Direct Repeat to which DRb is complementary.

4. A method according to claim 1, wherein the microorganism is *M tuberculosis, M bovis* or *M africanum.*

5. A method according to claim 1, wherein the primer has an oligonucleotide sequence capable of hybridizing to a consensus sequence of the Direct Repeat consisting of SEQ ID NO:2 in such a manner that amplification occurs under the circumstances of the amplification reaction used.

6. A method according to claim 3, wherein the primer DRa consists of SEQ ID NO:50 and DRb consists of SEQ ID NO:51.

7. A method of detection of a microorganism belonging to the *M tuberculosis* complex of microorganisms comprising 1) amplifying nucleic acid from a sample by the method according to claim 1, followed by 2) carrying out a hybridization test, wherein the amplification product is hybridized to an oligonucleotide probe or a plurality of different oligonucleotide probes, each oligonucleotide probe being homologous to a part of a spacer of the Direct Region of a microorganism belonging to the *M tuberculosis* complex whereby hybridization occurs to the amplified product if a nucleic acid sequence of said spacer was present in the sample prior to amplification, and 3) detecting any hybridized products.

8. A method according to claim 7, wherein said hybridization step is carried out without prior electrophoresis or separation of the amplified product.

9. A method according to claim 7, wherein the hybridization test is carried out using a number of oligonucleotide probes, said number comprising at least a number of oligonucleotides probes specific for the total spectrum of microorganisms it is desired to detect.

10. A method according to claim 7, wherein the microorganism belongs to the group *M tuberculosis* or *M bovis* or *M africanum.*

11. A method according to claim 7, wherein the oligonucleotide probe is at least seven oligonucleotides long and is a sequence complementary to a sequence selected from any of spacers 1–43 of *M tuberculosis* H37Rv and spacers 1–49 of *M bovis* BCG or is a sequence complementary to fragments or derivatives of said spacers, said oligonucleotide probe being capable of hybridizing to one of said spacers and comprising at least seven consecutive nucleotides homologous to one of said spacers.

12. A method according to claim 7, wherein the oligonucleotide probe is at least 7 oligonucleotides long and is a sequence complementary to any spacer common to *M tuberculosis* H37Rv and *M bovis* BCG, said oligonucleotide probe being capable of hybridizing to said spacer and comprising at least seven consecutive nucleotides exhibiting at least 60% homology to said spacer.

13. A method for differentiating the type of microorganisms belonging to the *M tuberculosis* complex in a sample, comprising carrying out the method according to claim 7, followed by comparison of the hybridization pattern obtained with a reference.

14. A method for differentiating the type of microorganism belonging to the *M tuberculosis* complex in a sample according to claim 13 wherein said reference is the hybridization pattern obtained with at least one strain of microorganism belonging to the *M tuberculosis* complex of microorganisms.

15. A method for differentiating the type of microorganism belonging to the *M tuberculosis* complex in a sample according to claim 13 wherein said reference is a source providing a list of spacer sequences and sources thereof.

16. A pair of primers wherein both primers comprise oligonucleotide sequences of at least 7 oligonucleotides and are complementary to a part of a Direct Repeat sequence of a microorganism belonging to the *M tuberculosis* complex of microorganisms, whereby hybridization occurs and subsequently elongation of the hybridized primer takes place, said primers being such that elongation in the amplification reaction occurs for one primer in the 5' direction and for the other primer in the 3' direction and wherein said oligonucleotide sequence comprises at least seven consecutive nucleotides homologous to said Direct Repeat sequence.

17. Primer pair according to claim 16, comprising one primer DRa capable of elongation in the 5' direction and another primer DRb capable of elongation in the 3' direction with DRa being complementary to a sequence of the Direct Repeat located to the 5' side of the sequence of the Direct Repeat to which DRb is complementary, the Direct Repeat being present in the Direct Region of a microorganism belonging to the group of *M tuberculosis* complex.

18. Primer pair according to claim 17, wherein DRa has sequence id. no. 50 and DRb has sequence id. no. 51.

19. Kit for carrying out a method of in vitro amplification of nucleic acid or for differentiating the type of microorganism belonging to the *M tuberculosis* complex in a sample, comprising a primer pair according to claim 16, and an oligonucleotide probe or a carrier, said carrier comprising at least 1 oligonucleotide probe specific for a spacer region of a microorganism of the group belonging to *M tuberculosis* complex, said oligonucleotide probe being an oligonucleotide probe of at least 7 nucleotides, said probe being homologous to any of the spacer sequences id no. 1–23 and 44–49 of *M bovis* BCG and id no. 35–43 of *M tuberculosis* H37Rv or to fragments or derivatives of said spacer sequences thereby to hybridize to said spacer sequence, said oligonucleotide probe comprising at least seven consecutive nucleotides homologous to said spacer sequence.

20. Kit for carrying out a method of in vitro amplification of nucleic acid or for differentiating the type of microorganism belonging to the *M tuberculosis* complex in a sample, comprising a primer pair according to claim 16, and a plurality of oligonucleotide probes or a carrier, said carrier comprising at least 1 oligonucleotide probe specific for a spacer region of a microorganism of the group belonging to *M tuberculosis* complex, said oligonucleotide probe being an oligonucleotide probe of at least 7 nucleotides, said probe being homologous to any of the spacer sequences id no. 1–23 and 44–49 of *M bovis* BCG and id no. 35–43 of *M tuberculosis* H37Rv or to fragments or derivatives of said spacer sequences thereby to hybridize to said spacer sequence, said oligonucleotide probe comprising at least seven consecutive nucleotides homologous to said spacer sequence.

* * * * *

SEQUENCE LISTING (1) GENERAL INFORMATION:

(iii) NUMBER OF SEQUENCES: 51

(2) INFORMATION FOR SEQ ID NO: 1:

(i) SEQUENCE CHARACTERISTICS:
        (A) LENGTH: 5519 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: M tuberculosis strain H37Rv DR cluster
            flanking IS6110

(xi) SEQUENCE DESCRIPTION: SEQ ID NO: 1:

| | | | | | |
|---|---|---|---|---|---|
| ACGCGTATAT | CGGTTTCCTA | CACCAGGATT | CACGAGGGCA | CGCAACGTTG | GCGAGCGACC | 60 |
| TCATGGAGGT | ATGGCGGGCG | CCGATCATCG | ATGACACCGT | ACTTCGATTG | ATCGCGGACG | 120 |
| GTGTGGTCGA | CACCCGGGCT | TTCAGCAAGA | ACTCCGACAC | GGGGGCCGTC | TTCGCGACAC | 180 |
| GGGAAGCCAC | ACGATCCATC | GCGCGCGCCT | TTTGTAATCG | AATCGCACGA | ACCGCCACCT | 240 |
| ACATCAAAGG | CGATCCTTAC | CGATACACTT | TTCAGTACGC | CCTCGACTTG | CAACTGCAAA | 300 |
| GCTCGTGCGT | GTTATTCGAA | GCCGGGGAAC | CCGTCGNGGT | CGTCGATATC | ACCTCCGAGC | 360 |
| CATCCGGAGC | CTAAATGCCC | ACTCGCAGCC | GTGAGGAGTA | CTTCAATCTC | CCGCTCAAAG | 420 |
| TGGACGAGTC | CAGCGGCACT | ATAGGCAAGA | TGTTCGTCCT | CGTAATATAC | GACATCAGCG | 480 |
| ACAACCGGCG | GCGGGCTTCA | CTTGCGAAGA | TCCTGGCCGG | GTTTGGCTAT | CGCGTCCAAG | 540 |
| AGTCCGCATT | CGAAGCGATG | CTGACGAAGG | GCCAGCTCGC | GAAACTAGTT | GCACGTATCG | 600 |
| ACCGCTTCGC | CATCGACTGC | GACAACATCC | GGATCTATAA | GATAAGAGGT | GTTGCGGCAG | 660 |
| TTACGTTCTA | CGGAAGGGGA | CGGCTTGTCA | GCGCAGAGGA | GTTTGTGTTC | TTTTGACATC | 720 |
| ATCAGCAGGC | ATTGTTACCA | CACGCTGGAC | GAATTGTCCA | TAGAGTCGTC | AGACCCAAAA | 780 |
| CCCCGAGAGG | GGACGGAAAC | TTAAAACCGT | GTTGTACTGC | AACCCGGAAT | TCTTGAACGT | 840 |
| CGTCAGACCC | AAAACCCCGA | GAGGGACGG | AAACCATAGA | GGGTCGCCGG | TTCTGGATCA | 900 |

-continued

```
CGCTCCCCTA GTCGTGTCGT CAGACCCAAA ACCCCGAGAG GGGACGGAAA CTTTTTGCCT    960

CATAATTGGG CGACAGCTTT TGACCAAGTC GTCAGACCCA AAACCCCGAG AGGGGACGGA   1020

AACTCGCAAG CGCCGTGCTT CCAGTGATCG CCTTCTAGTC GTCAGACCCA AAACCCCGAG   1080

AGGGGACGGA AACAACACCT CAGTAGCACG TCATACGCCG ACCAATCATC AGGTCGTCAG   1140

ACCCAAAACC CCGAGAGGGG ACGGAAACTT TTCTGACCAC TTGTGCGGGA TTAGCGGGCT   1200

TAGGTCGTCA GACCCAAAAC CCCGAGAGGG GACGGAAACA CCAATGCGTC GTCATTTCCG   1260

GCTTCAATTT CAGCCTGTCG TCAGACCCAA ACCCCGAGA GGGGACGGAA ACCTGAGGAG    1320

AGCGAGTACT CGGGGCTGCC GTCTGCGCTG GTCGTCAGAC CCAAAACCCC GAGAGGGGAC   1380

GGAAACGCGT GAAACCGCCC CCAGCCTCGC CGGGGCCGCC TAGGTCGTCA GACCCAAAAC   1440

CCCGAGAGGG GACGGAAACA CTCGGAATCC CATGTGCTGA CAGCGGATTC GCATGTCGTC   1500

AGACCCAAAA CCCCGAGAGG GGACGGAAAC CGGGCAGCGT TCGACACCCG CTCTAGTTGA   1560

CTTCCGGGTC GTCAGACCCA AAACCCCGAG AGGGGACGGA AACCAGGTGA GCAACGGCGG   1620

CGGCAACCTG GCGGCCACGG GTCGGTCGTC AGACCCAAAA CCCCGAGAGG GGACGGAAAC   1680

ATGGGATATC TGCTGCCCGC CCGGGGAGAT GCTGTCCGAG GTCGTCAGAC CCAAAACCCC   1740

GAGAGGGGAC GGAAACTTCG TCGACCATCA TTGCCATTCC CTCTCCCCAC GTGTCGTCAG   1800

ACCCAAAACC CCGAGAGGGG ACGGAAACTT GCGCCAACCC TTTCGGTGTG ATGCGGATGG   1860

TCGGCTCGGG TCGTCAGACC CAAAACCCCG AGAGGGACG GAAACCTTGA ATAACGCGCA    1920

GTGAATTTCG CGGATCAGAC CCAAAACCCC GAGAGGGGAC GGAAACATTC GCACGAGTTC   1980

CCGTCAGCGT CGTAAATCGC CAGTCGTCAG ACCCAAAACC CCGAGAGGGG ACGGAAACCC   2040

GGCAACAATC GCGCCGGCCC GCGCGGATGA CTCCGGTCGT CAGACCCAAA ACCCCGAGAG   2100

GGACGGAAA CCGCATGGAC CCGGGCGAGC TGCAGATGGT CCGGGAGGTC GTCAGACCCA    2160

AAACCCCGAG AGGGGACGGA AACTGGATTG CGCTAACTGG CTTGGCGCTG ATCCTGGTGG   2220

TCGTCAGACC CAAAACCCCG AGAGGGACG GAAACTTGGA GCGTGTCACC GCAGACGGCA    2280

CGATTGAGAC AAGTCGTCAG ACCCAAAACC CCGAGAGGGG ACGGAAACCC TCAGCTCAGC   2340

ATCGCTGATG CGGTCCAGCT CGTCCGTGTC GTCAGACCCA AAACCCCGAG AGGGGACGGA   2400

AACCCAACCT CACCGCCTGC TGGGTGAGAC GTGCTCGCCG CGAGTCGTCA GACCCAAAAC   2460

CCTGAACCGC CCCGGCATGT CCGGAGACTC CAGTTCTTGG AAAGGATGGG GTCATGTCAG   2520

GTGGTTCATC GAGGAGGTAC CCGCCGGAGC TGCGTGAGCG GGCGGTGCGG ATGGTCGCAG   2580

AGATCCGCGG TCAGCACGAT TCGGAGTGGG CAGCGATCAG TGAGGTCGCC CGTCTACTTG   2640

GTGTTGGCTG CGCGGAGACG GTGCGTAAGT GGGTGCGCCA GGCGCAGGTC GATGCCGGCG   2700

CACGGCCCGG GACCACGACC GAAGAATCCG CTGAGCTGAA GCGCTTAGCG GCGGGACAAC   2760

GCCGAATTGC GAAGGGCGAA CGCGATTTTA AGACCGCGT CGGCTTTCTT CGCGGCCGAG    2820

CTCGACCGGC CAGCACGCTA ATTAACGGTT CATCGCCGAT CATCAGGGCC ACCGCGAGGG   2880

CCCCGATGGT TTGCGGTGGG GTGTCGAGTC GATCTGCACA CAGCTGACCG AGCTGGGTGT   2940

GCCGATCGCC CCATCGACCT ACTACGACCA CATCAACCGG GAGCCCAGCC GCCGCGAGCT   3000

GCGCGATGGC GAACTCAAGG AGCACATCAG CCGCGTCCAC GCCGCCAACT ACGGTGTTTA   3060

CGGTGCCCGC AAAGTGTGGC TAACCCTGAA CCGTGAGGGC ATCGAGGTGG CCAGATGCAC   3120

CGTCGAACGG CTGATGACCA AACTCGGCCT GTCCGGGACC ACCCGCGGCA AAGCCCGCAG   3180

GACCACGATC GCTGATCCGG CCACAGCCCG TCCCGCCGAT CTCGTCCAGC GCCGCTTCGG   3240

ACCACCAGCA CCTAACCGGC TGTGGGTAGC AGACCTCACC TATGTGTCGA CCTGGGCAGG   3300
```

```
GTTCGCCTAC GTGGCCTTTG TCACCGACGC CTACGCGCAG GATCCTGGGC TGGCGGGTCG        3360

CTTCCACGAT GGCCACCTCC ATGGTCCTCG ACGCGATCGA GCAAGCCATC TGGACCCGCC        3420

AACAAGAAGG CGTACTCGAC CTGAAAGACG TTATCCACCA TACGGATAGG GGATCTCAGT        3480

ACACATCGAT CCGGTTCAGC GAGCGGCTCG CCGAGGCAGG CATCCAACCG TCGGTCGGAG        3540

CGGTCGGAAG CTCCTATGAC AATGCACTAG CCGAGACGAT CAACGGCCTA TACAAGACCG        3600

AGCTGATCAA ACCCGGCAAG CCCTGGCGGT CCATCGAGGA TGTCGAGTTG GCCACCGCGC        3660

GCTGGGTCGA CTGGTTCAAC CATCGCCGCC TCTACCAGTA CTGCGGCGAC GTCCCGCCGG        3720

TCGAACTCGA GGCTGCCTAC TACGCTCAAC GCCAGAGACC AGCCGCCGGC TGAGGTCTCA        3780

GATCAGAGAG TCTCCGGACT CACCGGGGCG GTTCACCCCG AGAGGGGACG GAAACTCGGG        3840

GAGCCGATCA GCGACCACCG CACCCTGTCA GTCGTNAGAC CCAAAACCCC GAGAGGGGAC        3900

GGAAACCTTC AGCACCACCA TCATCCGGCG CCTCAGCTCA GCATGTCGTC AGACCCAAAA        3960

CCCCGAGAGG GGACGGAAAC CCTTCGACGC CGGATTCGTG ATCTCTTCCC GCGGATAGGT        4020

CGTCAGACCC AAAACCCCGA GAGGGACGG AAACTGCCCC GGCGTTTAGC GATCACAACA        4080

CCAACTAATG GTCGTCAGAC CCAAAACCCC GAGAGGGAC GGAAACCAGC GAAATACAGG        4140

CTCCACGACA CGACCACAAC GCGTCGTCAG ACCCAAAACC CCGAGAGGGG ACGGAAACTC        4200

TTGACGATGC GGTTGCCCCG CGCCCTTTTC CAGCCGTCGT CAGACCCAAA ACCCCGAGAG        4260

GGGACGGAAA CAGGTTCGCG TCAGACAGGT TCGCGTCGAT CAAGTCCGGT CGTCAGACCC        4320

AAAACCCCGA GAGGGACGG AAACTTTATC ACTCCCGACC AAATAGGTAT CGGCGTGTTC        4380

AAGTCGTCAG ACCCAAAACC CCGAGAGGGG ACGGAAACAT TTTGAGCGCG AACTCGTCCA        4440

CAGTCCCCCT TTCAGGTCGT CAGACCCAAA ACCCCGAGAG GGGACGGAAA CGCCCCGTGG        4500

ATGGCGGATG CGTTGTGCGC GCAAGTGTCG TCAGACCCAA AACCCCGAGA GGGGACGGAA        4560

ACCCGACGAT GGCCAGTAAA TCGGCGTGGG TAACCGATCC GGGTCGTCAG ACCCAAAACC        4620

CCGAGAGGGG ACGGAAACTA GTACGCCATC TGTGCCTCAT ACAGGTCCAG TGCCCTGTCG        4680

TCAGACCCAA AACCCCGAGA GGGGACGGAA ACCTGACGGC ACGGAGCTTT CCGGCTTCTA        4740

TCAGGTAGTC GTCAGACCCA AAACCCCGAG AGGGGACGGA AACCCTCATG GTGGGACATG        4800

GACGAGCGCG ACTATCGGGG TCGTCGGACC CAAAACCCCG AGAGGGACG GAAACTGGAC        4860

GCAGAATCGC ACCGGGTGCG GGAGGTGCAG CAGTCGTCAG ACCCAAAACC CCGAGAGGGG        4920

ACGGAAACGC ATATCGCCCG CCACACCACA GCCACGCTAC TGCTCCATGT CCTCAGACCC        4980

AAAACCCCGA GAGGGACGG AAACACACCG CCGATGACAG CTATGTCCGA GTGACATCCT        5040

CCCAGTCGTC AGACCCAAAA CCACGAGAGG GGACGGAAAC TTGAACCGCC CTTCGCGCGG        5100

TGTTTCGGCC GTGCCCGAGT CGTCAGACCC AAAACCCCGA GAGGGACGG AAACTACGAC        5160

GACTGGGTCG CCACCGCGTC TGTCGACCTN GCATTCAGGA TGANCATGAT GGCGGCGTTG        5220

ACGGTGAGGA CGTTTGGTCA TGAAATGNNC NCGCCGGGAG ATGTCCGGCG GGTCGGTGG        5280

TGTTCGGGGT GTCGGTGTGG TGTTCAGTCT GCCGTGACTT CGGCGATGGC GGTGCGGNTG        5340

GTGGATTCGT CGACGATGGC CTTNTCGGCG GCGAAGGCGG CGACGAGGGC TTNCAGGGCG        5400

AGGTTGTTGA CCGCGCGGGG GTAGCCCCGN CTGGTCTGGT GGATCAACCC GATGGCGTCG        5460

TCGGAGAACA GGGCATCGTC GNGTCCGGCT ANCTTNAGGT TGTTGCGTAG GTAGCTTCC        5519
```

(2) INFORMATION FOR SEQ ID NO: 2:

(i) SEQUENCE CHARACTERISTICS:

(A) LENGTH: 36 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Consensus sequence of direct repeat of M.
                tuberculosis (xi) SEQUENCE DESCRIPTION: SEQ ID NO: 2:

GTCGTCAGAC CCAAAACCCC GAGAGGGGAC GGAAAC                                        36

(2) INFORMATION FOR SEQ ID NO: 3:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: primer for M.
                tuberculosis, spacer 01

(xi) SEQUENCE DESCRIPTION: SEQ ID NO: 3:

TTGTACTGCA ACCCGGAATT CTTGA                                                   25

(2) INFORMATION FOR SEQ ID NO: 4:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: primer for M.
                tuberculosis, spacer 02

(xi) SEQUENCE DESCRIPTION: SEQ ID NO: 4:

ATAGAGGGTC GCCGGTTCTG GATCA                                                   25

(2) INFORMATION FOR SEQ ID NO: 5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: primer for M.
                tuberculosis, spacer 03

(xi) SEQUENCE DESCRIPTION: SEQ ID NO: 5:

CCTCATAATT GGGCGACAGC TTTTG                                                   25

(2) INFORMATION FOR SEQ ID NO: 6:

(i) SEQUENCE CHARACTERISTICS:
            (A) LENGTH: 25 base pairs
            (B) TYPE: nucleic acid
            (C) STRANDEDNESS: single

```
       (D) TOPOLOGY: linear (ii) MOLECULE TYPE: cDNA (vi) ORIGINAL SOURCE:
        (A) ORGANISM: primer for M.
            tuberculosis, spacer 04

(xi) SEQUENCE DESCRIPTION: SEQ ID NO: 6:

CCGTGCTTCC AGTGATCGCC TTCTA                                        25

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 05

(xi) SEQUENCE DESCRIPTION: SEQ ID NO: 7:

ACGTCATACG CCGACCAATC ATCAG                                        25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 06

(xi) SEQUENCE DESCRIPTION: SEQ ID NO: 8:

TTTTCTGACC ACTTGTGCGG GATTA                                        25

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 07

(xi) SEQUENCE DESCRIPTION: SEQ ID NO: 9:

CGTCGTCATT TCCGGCTTCA ATTTC                                        25

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
        (A) ORGANISM: primer for M.
            tuberculosis, spacer 08

(xi) SEQUENCE DESCRIPTION: SEQ ID NO: 10:

GAGGAGAGCG AGTACTCGGG GCTGC                                              25

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 09

(xi) SEQUENCE DESCRIPTION: SEQ ID NO: 11:

CGTGAAACCG CCCCCAGCCT CGCCG                                              25

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 10

(xi) SEQUENCE DESCRIPTION: SEQ ID NO: 12:

ACTCGGAATC CCATGTGCTG ACAGC                                              25

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 11

(xi) SEQUENCE DESCRIPTION: SEQ ID NO: 13:

TCGACACCCG CTCTAGTTGA CTTCC                                              25

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.

tuberculosis, spacer 12

(xi) SEQUENCE DESCRIPTION: SEQ ID NO: 14:

GTGAGCAACG GCGGCGGCAA CCTGG        25

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 13

(xi) SEQUENCE DESCRIPTION: SEQ ID NO: 15:

ATATCTGCTG CCCGCCCGGG GAGAT        25

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 14

(xi) SEQUENCE DESCRIPTION: SEQ ID NO: 16:

GACCATCATT GCCATTCCCT CTCCC        25

(2) INFORMATION FOR SEQ ID NO: 17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 15

(xi) SEQUENCE DESCRIPTION: SEQ ID NO: 17:

GGTGTGATGC GGATGGTCGG CTCGG        25

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 16

(xi) SEQUENCE DESCRIPTION: SEQ ID NO: 18:

```
CTTGAATAAC GCGCAGTGAA TTTCG                                              25
```

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 17

(xi) SEQUENCE DESCRIPTION: SEQ ID NO: 19:

```
CGAGTTCCCG TCAGCGTCGT AAATC                                              25
```

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 18

(xi) SEQUENCE DESCRIPTION: SEQ ID NO: 20:

```
GCGCCGGCCC GCGCGGATGA CTCCG                                              25
```

(2) INFORMATION FOR SEQ ID NO: 21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 19

(xi) SEQUENCE DESCRIPTION: SEQ ID NO: 21:

```
CATGGACCCG GGCGAGCTGC AGATG                                              25
```

(2) INFORMATION FOR SEQ ID NO: 22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 20

(xi) SEQUENCE DESCRIPTION: SEQ ID NO: 22:

```
TAACTGGCTT GGCGCTGATC CTGGT                                              25
```

(2) INFORMATION FOR SEQ ID NO: 23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 21

(xi) SEQUENCE DESCRIPTION: SEQ ID NO: 23:

ACCGCAGACG GCACGATTGA GACAA                                    25

(2) INFORMATION FOR SEQ ID NO: 24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 22

(xi) SEQUENCE DESCRIPTION: SEQ ID NO: 24:

AGCATCGCTG ATGCGGTCCA GCTCG                                    25

(2) INFORMATION FOR SEQ ID NO: 25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 23

(xi) SEQUENCE DESCRIPTION: SEQ ID NO: 25:

CCGCCTGCTG GGTGAGACGT GCTCG                                    25

(2) INFORMATION FOR SEQ ID NO: 26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 24

(xi) SEQUENCE DESCRIPTION: SEQ ID NO: 26:

GATCAGCGAC CACCGCACCC TGTCA                                    25

(2) INFORMATION FOR SEQ ID NO: 27:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
             tuberculosis, spacer 25

(xi) SEQUENCE DESCRIPTION: SEQ ID NO: 27:

CTTCAGCACC ACCATCATCC GGCGC                                              25

(2) INFORMATION FOR SEQ ID NO: 28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
             tuberculosis, spacer 26

(xi) SEQUENCE DESCRIPTION: SEQ ID NO: 28:

GGATTCGTGA TCTCTTCCCG CGGAT                                              25

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
             tuberculosis, spacer 27

(xi) SEQUENCE DESCRIPTION: SEQ ID NO: 29:

TGCCCCGGCG TTTAGCGATC ACAAC                                              25

(2) INFORMATION FOR SEQ ID NO: 30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
             tuberculosis, spacer 28

(xi) SEQUENCE DESCRIPTION: SEQ ID NO: 30:

AAATACAGGC TCCACGACAC GACCA                                              25

(2) INFORMATION FOR SEQ ID NO: 31:

(i) SEQUENCE CHARACTERISTICS:
        (A) LENGTH: 25 base pairs
        (B) TYPE: nucleic acid
```

```
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 29

(xi) SEQUENCE DESCRIPTION: SEQ ID NO: 31:

GGTTGCCCCG CGCCCTTTTC CAGCC                                              25

(2) INFORMATION FOR SEQ ID NO: 32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 30

(xi) SEQUENCE DESCRIPTION: SEQ ID NO: 32:

TCAGACAGGT TCGCGTCGAT CAAGT                                              25

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 31

(xi) SEQUENCE DESCRIPTION: SEQ ID NO: 33:

GACCAAATAG GTATCGGCGT GTTCA                                              25

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 32

(xi) SEQUENCE DESCRIPTION: SEQ ID NO: 34:

CGCGAACTCG TCCACAGTCC CCCTT                                              25

(2) INFORMATION FOR SEQ ID NO: 35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear
```

-continued

```
    (ii) MOLECULE TYPE: cDNA (vi) ORIGINAL SOURCE:
         (A) ORGANISM: primer for M.
             tuberculosis, spacer 33

(xi) SEQUENCE DESCRIPTION: SEQ ID NO: 35:

CGTGGATGGC GGATGCGTTG TGCGC                                              25

(2) INFORMATION FOR SEQ ID NO: 36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 34

(xi) SEQUENCE DESCRIPTION: SEQ ID NO: 36:

GACGATGGCC AGTAAATCGG CGTGG                                              25

(2) INFORMATION FOR SEQ ID NO: 37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 35

(xi) SEQUENCE DESCRIPTION: SEQ ID NO: 37:

CGCCATCTGT GCCTCATACA GGTCC                                              25

(2) INFORMATION FOR SEQ ID NO: 38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: primer for M.
             tuberculosis, spacer 36

(xi) SEQUENCE DESCRIPTION: SEQ ID NO: 38:

GGAGCTTTCC GGCTTCTATC AGGTA                                              25

(2) INFORMATION FOR SEQ ID NO: 39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
```

(A) ORGANISM: primer for M.
            tuberculosis, spacer 37

(xi) SEQUENCE DESCRIPTION: SEQ ID NO: 39:

ATGGTGGGAC ATGGACGAGC GCGAC                                        25

(2) INFORMATION FOR SEQ ID NO: 40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 38

(xi) SEQUENCE DESCRIPTION: SEQ ID NO: 40:

CGCAGAATCG CACCGGGTGC GGGAG                                        25

(2) INFORMATION FOR SEQ ID NO: 41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 39

(xi) SEQUENCE DESCRIPTION: SEQ ID NO: 41:

ATATCGCCCG CCACACCACA GCCAC                                        25

(2) INFORMATION FOR SEQ ID NO: 42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 40

(xi) SEQUENCE DESCRIPTION: SEQ ID NO: 42:

CGCCGATGAC AGCTATGTCC GAGTG                                        25

(2) INFORMATION FOR SEQ ID NO: 43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer 41

(xi) SEQUENCE DESCRIPTION: SEQ ID NO: 43:

TTCGCGCGGT GTTTCGGCCG TGCCC                                              25

(2) INFORMATION FOR SEQ ID NO: 44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            bovis BCG, spacer B1

(xi) SEQUENCE DESCRIPTION: SEQ ID NO: 44:

TTGACCTCGC CAGGAGAGAA GATCA 25

(2) INFORMATION FOR SEQ ID NO: 45:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: primer for M. bovis BCG, spacer B2

(xi) SEQUENCE DESCRIPTION: SEQ ID NO: 45:

TCGATGTCGA TGTCCCAATC GTCGA 25

(2) INFORMATION FOR SEQ ID NO: 46:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: primer for M. bovis BCG, spacer B3

(xi) SEQUENCE DESCRIPTION: SEQ ID NO: 46:

GACATGACGG CGGTGCCGCA CTTGA 25

(2) INFORMATION FOR SEQ ID NO: 47:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: primer for M. bovis BCG, spacer B4

(xi) SEQUENCE DESCRIPTION: SEQ ID NO: 47:

AAGTCACCTC GCCCACACCG TCGAA 25

(2) INFORMATION FOR SEQ ID NO: 48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            bovis BCG, spacer B5

(xi) SEQUENCE DESCRIPTION: SEQ ID NO: 48:

TCCGTACGCT CGAAACGCTT CCAAC                                  25

(2) INFORMATION FOR SEQ ID NO: 49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            bovis BCG, spacer B6

(xi) SEQUENCE DESCRIPTION: SEQ ID NO: 49:

CGAAATCCAG CACCACATCC GCAGC                                  25

(2) INFORMATION FOR SEQ ID NO: 50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer DRa (xi) SEQUENCE DESCRIPTION: SEQ ID NO: 50:

CCGAGAGGGG ACGGAAAC                                            18

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: primer for M.
            tuberculosis, spacer DRb (xi) SEQUENCE DESCRIPTION: SEQ ID NO: 51:

GGTTTTGGGT CTGACGAC                                              18